(12) United States Patent
Palmese et al.

(10) Patent No.: US 7,953,612 B1
(45) Date of Patent: May 31, 2011

(54) SYSTEM AND METHOD FOR PROVIDING A SEARCHABLE DATABASE OF SURGICAL INFORMATION

(75) Inventors: Nicholas Palmese, Hot Springs, AR (US); Thomas T. Jeneby, San Antonio, TX (US); David H. Bornstein, New York, NY (US)

(73) Assignee: Ecomglobalmedical Research & Development, Inc, San Antonio, TX (US)

( * ) Notice: Subject to any disclaimer, the term of this patent is extended or adjusted under 35 U.S.C. 154(b) by 988 days.

(21) Appl. No.: 11/458,069

(22) Filed: Jul. 17, 2006

(51) Int. Cl.
*G06Q 10/00* (2006.01)

(52) U.S. Cl. ............ 705/3; 128/922; 128/923; 707/722; 707/769; 715/968

(58) Field of Classification Search .................. 705/2–3; 128/922–923; 707/722, 769; 715/968
See application file for complete search history.

(56) References Cited

U.S. PATENT DOCUMENTS

| | | | |
|---|---|---|---|
| 4,058,832 A | 11/1977 | Vagi | |
| 4,058,833 A | 11/1977 | Meyer | |
| 4,165,520 A | 8/1979 | Wessler et al. | |
| 4,196,447 A | 4/1980 | Dalke | |
| 4,283,736 A | 8/1981 | Morio et al. | |
| 4,491,873 A | 1/1985 | Takayama | |
| 4,531,161 A | 7/1985 | Murakoshi | |
| 4,555,803 A | 11/1985 | Hirose | |
| 4,563,701 A | 1/1986 | Gilath et al. | |
| 4,571,700 A | 2/1986 | Emry, Jr. et al. | |
| 4,587,635 A | 5/1986 | Hashimoto et al. | |
| 4,587,663 A | 5/1986 | Matsuoka et al. | |
| 4,598,369 A | 7/1986 | Wang et al. | |
| 4,601,003 A | 7/1986 | Yoneyama et al. | |
| 4,607,290 A | 8/1986 | Murakami | |
| 4,653,021 A | 3/1987 | Takagi | |
| 4,658,299 A | 4/1987 | Tanaka et al. | |
| 4,661,988 A | 4/1987 | Shimizu | |
| 4,674,064 A | 6/1987 | Vaughn | |
| 4,695,895 A | 9/1987 | Nagashima | |
| 4,695,975 A | 9/1987 | Bedrij | |

(Continued)

FOREIGN PATENT DOCUMENTS

WO WO2008003095 A2 1/2008

(Continued)

OTHER PUBLICATIONS

Welke et al. ("Validity of The Society of Thoracic Surgeons National Adult Cardiac Surgery Database", Ann Thorac Surg 2004;77:1137-9).*

(Continued)

*Primary Examiner* — Gerald J. O'Connor
*Assistant Examiner* — Mark Holcomb
(74) *Attorney, Agent, or Firm* — Cox Smith Matthews Incorporated

(57) ABSTRACT

Systems and methods of creating, managing, and using a database comprising surgical data may involve receiving input signals from a plurality of surgical data sources, the input signals being representative of surgical data associated with a plurality of patients, storing the surgical data in the database, and sending one or more output signals to one or more authorized users in response to one or more queries, the output signals being representative of one or more portions of the surgical data. Among other uses, the systems and methods may be used to improve the performance of surgical procedures, rate surgeons, train surgeons, and establish insurance rates for surgeons and patients.

6 Claims, 38 Drawing Sheets

U.S. PATENT DOCUMENTS

| | | | |
|---|---|---|---|
| 4,724,495 A | 2/1988 | Hedberg et al. | |
| 4,758,980 A | 7/1988 | Tsunekawa et al. | |
| 4,760,458 A | 7/1988 | Watanabe et al. | |
| 4,764,870 A | 8/1988 | Haskin | |
| 4,768,099 A | 8/1988 | Mukai | |
| 4,817,050 A | 3/1989 | Komatsu et al. | |
| 4,910,609 A | 3/1990 | Nicholas et al. | |
| 5,012,405 A | 4/1991 | Nishikado et al. | |
| 5,036,315 A | 7/1991 | Gurley | |
| 5,040,142 A | 8/1991 | Mori et al. | |
| 5,179,651 A | 1/1993 | Taaffe et al. | |
| 5,272,625 A | 12/1993 | Nishihara et al. | |
| 5,291,401 A | 3/1994 | Robinson | |
| 5,321,520 A | 6/1994 | Inga et al. | |
| 5,384,643 A | 1/1995 | Inga et al. | |
| 5,416,602 A | 5/1995 | Inga et al. | |
| 5,469,353 A | 11/1995 | Pinsky et al. | |
| 5,513,101 A | 4/1996 | Pinsky et al. | |
| 5,655,084 A | 8/1997 | Pinsky et al. | |
| 5,715,823 A | 2/1998 | Wood et al. | |
| 5,802,518 A | 9/1998 | Karaev et al. | |
| 5,810,747 A | 9/1998 | Brudny et al. | |
| 5,815,156 A | 9/1998 | Takeuchi | |
| 5,836,877 A | 11/1998 | Zavislan | |
| 5,851,186 A | 12/1998 | Wood et al. | |
| 5,857,967 A | 1/1999 | Frid et al. | |
| 5,949,491 A | 9/1999 | Callahan et al. | |
| 6,006,191 A | 12/1999 | DiRienzo | |
| 6,032,120 A | 2/2000 | Rock et al. | |
| 6,041,315 A * | 3/2000 | Pollin | 705/45 |
| 6,064,490 A | 5/2000 | Minamizawa | |
| 6,101,536 A | 8/2000 | Kotani et al. | |
| 6,157,675 A | 12/2000 | Mitsuhashi et al. | |
| 6,247,004 B1 | 6/2001 | Moukheibir | |
| 6,608,930 B1 | 8/2003 | Agnihotri et al. | |
| 6,792,401 B1 | 9/2004 | Nigro et al. | |
| 6,909,795 B2 * | 6/2005 | Tecotzky et al. | 382/128 |
| 6,937,766 B1 | 8/2005 | Wilf et al. | |
| 7,289,651 B2 * | 10/2007 | Vining et al. | 382/128 |
| 7,388,972 B2 * | 6/2008 | Kitson | 382/128 |
| 7,394,946 B2 * | 7/2008 | Dewaele | 382/276 |
| 7,542,791 B2 * | 6/2009 | Mire et al. | 600/407 |
| 2001/0011301 A1 | 8/2001 | Sato et al. | |
| 2001/0032246 A1 | 10/2001 | Fardella et al. | |
| 2001/0041991 A1 | 11/2001 | Segal et al. | |
| 2002/0186818 A1 | 12/2002 | Arnaud et al. | |
| 2002/0198454 A1 | 12/2002 | Seward et al. | |
| 2003/0187689 A1 | 10/2003 | Barnes et al. | |
| 2004/0122705 A1 * | 6/2004 | Sabol et al. | 705/2 |
| 2004/0230458 A1 | 11/2004 | Takayama et al. | |
| 2004/0249675 A1 * | 12/2004 | Stark et al. | 705/2 |
| 2005/0020903 A1 | 1/2005 | Krishnan et al. | |
| 2005/0192838 A1 | 9/2005 | Jones et al. | |
| 2005/0228270 A1 * | 10/2005 | Lloyd et al. | 600/424 |
| 2005/0281373 A1 | 12/2005 | Both et al. | |
| 2008/0002893 A1 | 1/2008 | Vincent et al. | |
| 2008/0002914 A1 | 1/2008 | Vincent et al. | |
| 2008/0002916 A1 | 1/2008 | Vincent et al. | |

FOREIGN PATENT DOCUMENTS

| | | |
|---|---|---|
| WO | PCT/US2007/072578 | 1/2009 |

OTHER PUBLICATIONS

Wheeless' Textbook of Orthopaedics, as available on Apr. 14, 2005 (viewable at http://web.archive.org/web/20050414202400/http://www.wheelessonline.com/ortho/surgical_technique_for_tkr ).*

Orthogate's Orthopaedic Surgery Topics database as available on Feb. 5, 2003 (viewable at http://web.archive.org/web/20030215184201/owl.orthogate.org/topics.html ).*

Pulido, et al., "Developing and Implementing an Orthopaedic Outcomes Program A Step-By-Step Guide," Orthopaedic Nursing, Mar./Apr. 2008, vol. 27, No. 2, pp. 94-100 (7 pages).

Stulberg, et al., "Columbus Primary Total Knee Replacement: A 2-to 4-Year Follow-up of the Use of Intraoperative Navigation-derived Data to predict Pre- and Postoperative Function," Orthopedics, Oct. 2008 Supplement, vol. 31, No. 10, pp. 51-56 (7 pages).

McKee, Jennie, "U.S. Joint Registry Gets Underway," American Academy of Orthopaedic Surgeons, 2010 Annual Meeting News, Mar. 10-13, 2010; http://www.aaos.org/news/acadnews/2010/AAOS12.3.12.asp (4 pages).

Hayashi, Annie, "National Joint Registry Legislation Introduced," AAOS Now, Jul. 2009 Issue, http://www.aaos.org/news/aaosnow/jul09/cover1.asp (4 pages).

Novicoff, et al., "2010 Annual Meeting Poster Presentations, Primary TKA: State of the Science and Comparison of Navigated vs. Manual Techniques," American Academy of Orthopaedic Surgeons, http://www.aaos.org/education/anmeet/anmt2010/poster/poster.cr (2 pages).

Haralson, III, Robert H., "The Advantages of the Quality Initiative," American Academy of Orthopaedic Surgeons, AAOS Now, Jul. 2008 Issue, http://www.aaos.org/news/aaosnow/jul08/reimbursement5.asp (2 pages).

American Academy of Orthopaedic Surgeons, "Surgeon on the Street-what developments in your field do you see as having the greatest impact on clinical practice in the upcoming years/future?" AAOS Now, Nov. 2009 Issue, http://www.aaos.org/news/aaosnow/nov09)yourassos12.asp (2 pages).

American Academy of Orthopaedic Surgeons, "SpotCheck: The role of CAS in TKA," AAOS Now, Mar. 2009 Issue; http://www.aaos.org/news/aaosnow/mar09/clinical16.asp (3 pages).

Hayashi, Annie, "Reframing the debate on computer-navigated TKA," American Academy of Orthopaedic Surgeons, AAOS Now, Oct. 2008 Issue; http://www.aaos.org/news/aaosnow/oct08/clinical10.asp (2 pages).

Hayashi, Annie, "Putting computer navigation to the test," American Academy of Orthopaedic Surgeons, AAOS Now, Aug. 2008 Issue, http://www.aaos.org/news/aaosnow/aug08/research4.asp (3 pages).

Flint, et al., "From Pong to CAOS," American Academy of Orthopaedic Surgeons, AAOS Now, Sep. 2007 Issue, http://www.aaos.org/news/bulletin/sep07/reimbursement3.asp (4 pages).

Pollack, "Computer-assisted TKAs yield better outcomes," American Academy of Orthopaedic Surgeons, AAOS Now, Apr. 2009 Issue, http://www.aaos.org/news/aaosnow/apr09/clinical6.asp (2 pages).

Porucznik, Mary Ann, "Computer navigation: Does it make you a better TKA surgeon?," American Academy of Orthopaedic Surgeons, AAOS Now, Jan./Feb. 2007, http://www.aaos.org/news/bulletin/janfeb07/clinical7.asp (4 pages).

Rogers, Carolyn, "AAOS supports research on many fronts," American Academy of Orthopaedic Surgeons, AAOS Now, May 2007 Issue, http://www.aaos.org/news/bulletin/may07/research6.asp (3 pages).

Colwell, et al., "2009 Annual Meeting Scientific Exhibits—Initiating a Multi-Subspecialty Orthopaedic Outcomes Program and Utilizing Data to Guide Practice," American Academy of Orthopaedic Surgeons, http://www.aaos.org/education/anmeet/anmt2009/se/sciexhibit.cr (2 pages).

* cited by examiner

Extension
Alignment

Before
Operation

Valgus 0.4°

Extension
Gap 21.5 mm

After
Operation

Valgus 2.5°

Extension
Gap 22.8 mm

Fig. 17

Before
Fig. 20
Before
Fig. 21
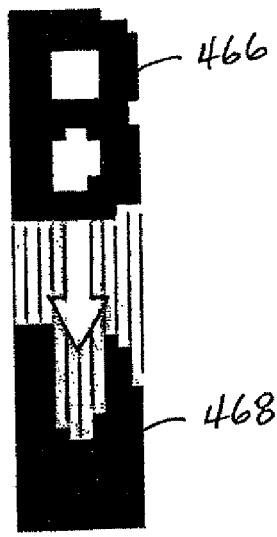
Fig. 22
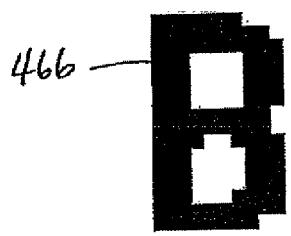 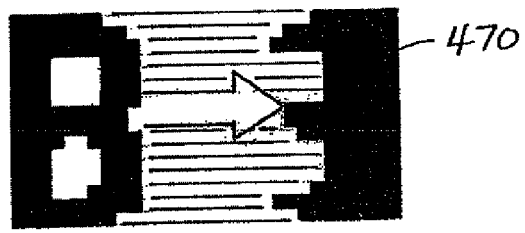
Fig. 23 array = 0, 0, 0, 0, 0, 0, 0, 0, 0, 0, 16, 16, 8, 7, 7, 9, 15, 14, 11, 0, 0, 0, 0, 8, 10, 7, 6, 6, 6, 8, 9, 9, 6, 6, 6, 6, 10, 9, 7 ignored      ignored

_542_

ORUPLOAD

(Open chat window)—545            Welcome Joe Crespo

SEARCH                          554 — clear form
Dates
    From [ALL]  544   [ALL]  546         [set date...]  
    to [ALL]          [ALL]                      552
        548            550    555
Data  556
    Extension Gap [ALL] to [ALL] — 558   (Saved searches)
    Flexion Gap [ALL] to 560 [ALL] — 562   edit saved searches
    Gap Differential [ALL] to 564 [ALL] — 566   (Compare saved searches)
    Mechanical Alignment [ALL] to 568 [ALL] Type [Both]       565
    Treatment Side [Both]                 570        572
        574
Registration            576
    Gender [Both]
    Age [ ] 578 to [ ] — 580
    Height [ALL] to 582 [ALL] — 584
    Weight [ALL] to 586 [ALL] — 588
    Analysis [ALL] 590
    Diseases [ALL] 592              — 594
Keyword Search
    Keyword [         ] 596 in [Patient ID] — 598
Sorting
    Sort by [Date of Treatment] 600  [Ascending] 602

[ SEARCH ] — 604

Fig. 36

Welcome Joe Crespo

SEARCH          refine search | new search
Summary          hide summary Search Criteria     Statistics

| | | Within Date Range | | All Dates | |
|---|---|---|---|---|---|
| | Averages | Personal (7) | Industry (46) | Personal (118) | Industry (570) |
| | Extension Gap | 7.73mm | 6.29mm | 5.39mm | 5.08mm |
| | Flexion Gap | 21.13mm | 15.41mm | 17.20mm | 16.95mm |
| | Gap Differential | 13.54mm | 10.38mm | 12.76mm | 12.81mm |
| | Mechanical Alignment | 4.23° | 4.10° | 4.26° | 4.16° |

Date Range Jan 06 - Feb 06
Extension Gap 0mm - 10mm
Flexion Gap ALL
Gap Differential ALL
Mechanical Alignment ALL
Treatment Side Both
Keyword N/A
Sort by Date of Treatment (asc)

Results          displaying 1 - 7 of 7 1

| Patient ID / Date | Fin. Alignment | | Fin. Gap Dif. | Fin. Flexion | Beg. Flexion | Beg. Ext |
|---|---|---|---|---|---|---|
| CC_CD6-2006-01-01_GHIHHSQU<br>Date: Jan 01 06 | 6.7° | Valgus | 9.3mm | 10.1mm | 0.2° | 0.8° |
| PP_CD2-2006-01-03_HS792GF<br>Date: Jan 03 06 | 6.2° | Valgus | 7.9mm | 26.2mm | 0.2° | 0.6° |
| VV_CD8-2006-01-04_KW3SJQCP<br>Date: Jan 04 06 | 1.3° | Valgus | 8.8mm | 16.9mm | 0.2° | 1.0° |
| SS_CD2-2006-01-06_D2869KDF<br>Date: Jan 06 06 | 8.3° | Valgus | 8.5mm | 24.6mm | 0.2° | 2.2° |
| PP_CD6-2006-01-07_ZH2KPAPD<br>Date: Jan 07 06 | 4.7° | Varus | 5.5mm | 5.0mm | 0.2° | 0.4° |
| AA_CD1-2006-01-28_ELE2EBMU<br>Date: Jan 28 06 | 0.7° | Varus | 5.9mm | 30.9mm | 0.3° | 8.0° |
| CC_CD2-2006-01-30_ZV3KWX5T<br>Date: Jan 30 06 | 1.7° | Varus | 8.2mm | 34.2mm | 0.2° | 6.0° | displaying 1 - 7 of 7 1

Fig. 37

```
Results from OR Upload search conducted on Jul 17 2006 at 2:09 pm - Message (Plain Text)
File  Edit  View  Insert  Format  Tools  Actions  Help
Reply | Reply to All | Forward | ...
E-mail Auto-link | Link to Record From:
To:
Cc:
Subject:  Results from OR Upload search conducted on Jul 17 2006 at 2:09 pm Search Criteria
---------------------------------
Date Range: Jan 06 - Jun 06
Treatment Side: Left
---------------------------------

Personal Statistics (within date range)
---------------------------------
Extension Gap: 17.25mm
Flexion Gap: 18.07mm
Gap Differential: 11.25mm
Mechanical Alignment: 4.24deg
---------------------------------

Industry-Wide Statistics (within date range)
---------------------------------
Extension Gap: 17.56mm
Flexion Gap: 17.67mm
Gap Differential: 11.45mm
Mechanical Alignment: 4.20deg
---------------------------------

Personal Statistics (all dates)
---------------------------------
Extension Gap: 17.20mm
Flexion Gap: 17.23mm
Gap Differential: 11.03mm
Mechanical Alignment: 4.01deg
---------------------------------

Industry-Wide Statistics (all dates)
---------------------------------
Extension Gap: 17.13mm
Flexion Gap: 17.54mm
Gap Differential: 11.33mm
Mechanical Alignment: 4.09deg
---------------------------------
```

Fig. 41

SYSTEM AND METHOD FOR PROVIDING A SEARCHABLE DATABASE OF SURGICAL INFORMATION

CROSS-REFERENCE TO RELATED APPLICATIONS

Not applicable.

FIELD

This application relates to information technology in the field of surgery.

BACKGROUND

In the field of surgery, various information technology systems are known, and a wide variety of data is collected during the course of a given surgical procedure. However, to date, the data that is collected during surgical procedures is not utilized to its full potential. Indeed, in the field of orthopedic surgery, for example, many compact disks (CDs) containing surgical data are generated and never used at all, except perhaps for archive purposes. Additionally, many types of information pertaining to a given patient's surgical procedure presently are stored only in a surgeon's brain and thus are not available for the benefit of others. Therefore, there is a need in the art for a system and method of collecting surgical data that will allow multiple surgeons, patients, hospitals, medical companies, and other users to realize the value of such information.

SUMMARY

Systems and methods of creating, managing, and using a database comprising surgical data may involve receiving input signals from a plurality of surgical data sources, the input signals being representative of surgical data associated with a plurality of patients, storing the surgical data in the database, and sending one or more output signals to one or more authorized users in response to one or more queries, the output signals being representative of one or more portions of the surgical data. Among other uses, the systems and methods may be used to improve the performance of surgical procedures, rate surgeons, train surgeons, and establish insurance rates for surgeons and patients.

BRIEF DESCRIPTION OF THE DRAWINGS

FIG. 17 is a schematic diagram of the highlighted portion of FIG. 15 broken down line by line.

FIG. 20 is a schematic diagram of the first line of text of FIG. 16.

FIG. 21 is a schematic diagram of the text of FIG. 20 showing a bounded area for each character.

FIG. 22 is a schematic diagram of an X-axis histogram of the first character of the text of FIG. 21.

FIG. 23 is a schematic diagram of a Y-axis histogram of the first character of the text of FIG. 21.

FIG. 36 is a screen shot of a search screen of a graphical user interface for performing queries of a surgical database.

FIG. 37 is a screen shot of a search results screen generated by the graphical user interface of FIG. 36.

FIG. 41 is a sample email message that may be sent.

DETAILED DESCRIPTION

Figure 1:
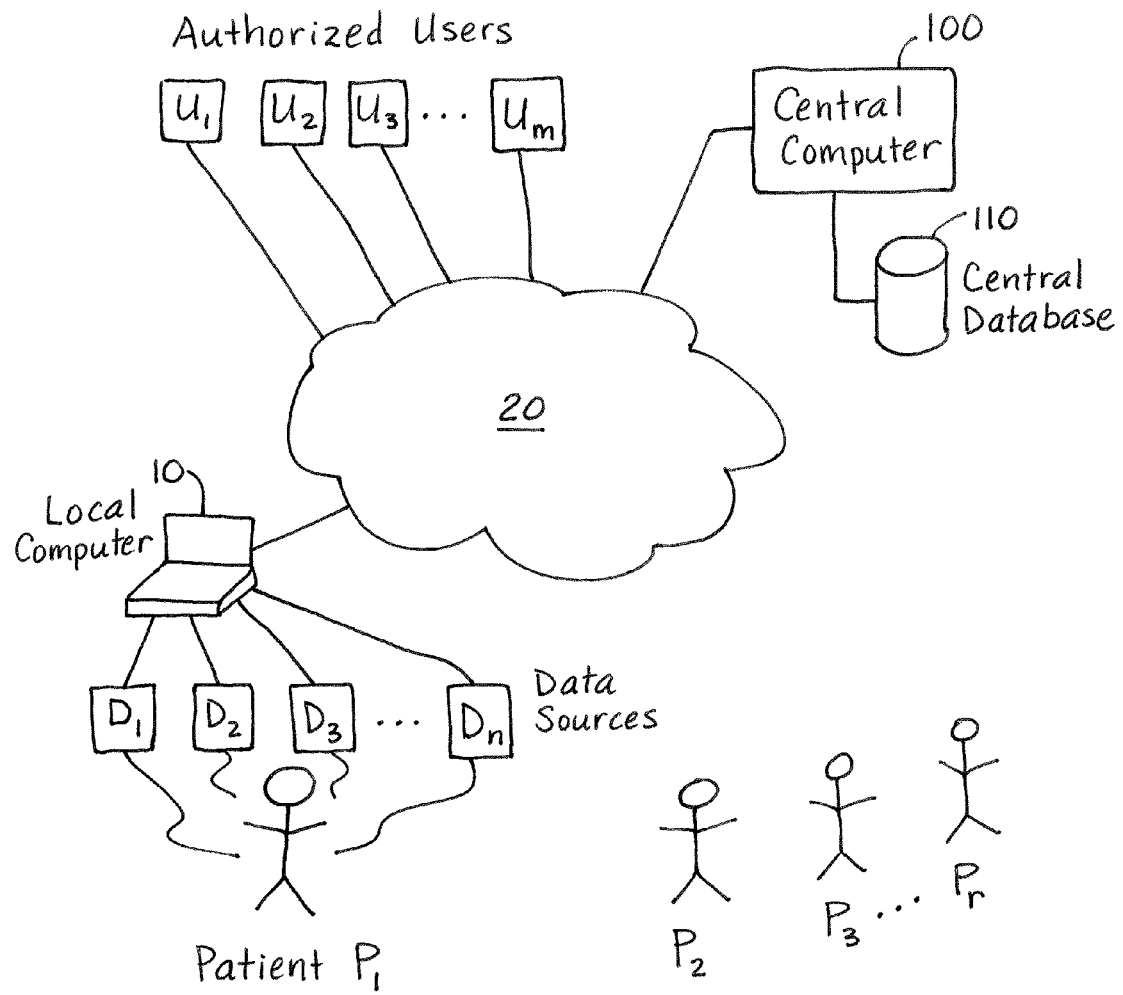
FIG. 1 is a schematic diagram of a system for collecting and managing surgical data.

As used herein, the following terms should be understood to have the indicated meanings When an item is introduced by "a" or "an," it should be understood to mean one or more of that item.

"Authorized user" means a person who is permitted to access one or more portions of a database.

"Communication" means the transmission of one or more signals from one point to another point. Communication between two objects may be direct, or it may be indirect through one or more intermediate objects.

"Comprises" means includes but is not limited to.

"Comprising" means including but not limited to.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

"Computer program" means a list of instructions that may be executed by a computer to cause the computer to operate in a desired manner.

"Computer readable medium" means an article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

"Data" means information.

"Database" means a collection of data embodied in at least one computer readable medium and organized in a suitable way to permit a computer to select one or more desired pieces of such data.

"Derived data" means information generated or obtained as a result of performing one or more operations using one or more pieces of raw data.

"Having" means including but not limited to.

"Optical character recognition" means identification of recorded characters by a machine using light-sensitive detectors.

"Patient" means a human being or an animal on which a surgical procedure has been performed or is to be performed.

"Plurality" means two or more.

"Query" means a request for information from a database.

"Raw data" means information in its originally acquired form.

"Signal" means a detectable physical phenomenon that is capable of conveying information. A signal may include but is not limited to an electrical signal, an electromagnetic signal, an optical signal, an acoustic signal, or a combination thereof.

"Surgical data" means information related to a surgical procedure performed or to be performed on a patient. By way of example, surgical data may include but is not limited to information regarding the patient, such as the patient's name, genus, species, identification number, birth date, age, height, weight, gender, heart rate, temperature, blood pressure, blood oxygen level, medical condition, medical history, diagnosis, genetic history, pre-surgery range of motion, and other characteristics of the patient; information regarding the surgical procedure, such as the type of surgery, date and time of surgery, location of surgery, duration of surgery, type of anesthesia used, time under anesthesia, blood loss, fluids injected, personnel involved, materials and equipment used, body parts operated on, sizes and materials of implants used, location and orientation of implants installed, and other treatment information; information regarding the results of the surgical procedure, such as post-surgery range of motion, pain levels, pain medication used, movement or loosening or degradation of implants, instances of repeated or additional operations, and elapsed time between operations; and any other information that may be collected in connection with the patient and the surgical procedure, whether before, during, or after the surgical procedure. Depending on the particular type of surgical data, it may be fixed or it may vary over time. Surgical data may comprise raw data, derived data, or a combination thereof. Surgical data may have any suitable form or format, such as alphanumeric text, pictorial or graphic images, audio, video, and other types of data.

"Surgical data source" means a machine, instrument, or other device capable of collecting or generating one or more pieces of surgical data and transmitting one or more signals representative of such one or more pieces of surgical data. By way of example, a surgical data source may include but is not limited to a computer, thermometer, heart rate sensor, blood pressure sensor, pulse oximeter, weight scale, height scale, timer, bar code scanner, fluid flow meter, x-ray machine, magnetic resonance imaging machine, acoustic imaging machine, or combination thereof. A surgical data source may receive input in any desired manner, such as by manual data entry via a keyboard, mouse, track ball, or other manual input device; by voice recognition; by one or more sensors or transducers, such as piezoelectric sensors, antennas or other electromagnetic wave detectors, acoustic sensors, light sensors, or thermocouples or other temperature sensors; or by any other desired manner.

"Surgical procedure" means any medical undertaking in which a patient is treated for a disease or condition by one or more operative or manual procedures. A surgical procedure may or may not involve one or more incisions. If an incision is made, it may be made by any suitable means, such as a scalpel, laser beam, or other cutting or puncturing instrument, for example. By way of example, surgical procedures may include but are not limited to the following types of surgery: ear, nose, and throat; general; neurological; obstetrics/gynecology (OB/GYN); ophthalmological; orthopedic; cardiac; cranial; pulmonary; thoracic; dental; plastic; urological; and vascular.

"Unrelated" means not affiliated with the same medical practice, hospital, laboratory, research institution, or other business entity.

As shown in FIG. 1, a system for populating and managing a surgical database may have a central computer 100 and a central database 110. Each of central computer 100 and central database 110 may comprise one or more units of hardware, which may or may not be located at the same geographic location. Central database 110, which may be integral to or separate from central computer 100, may serve as a searchable repository for a large volume of surgical data associated with a plurality of patients $P_1$-$P_n$. Central database 110 may be a relational database or any other suitable type of database. The patients for whom surgical data is collected in central database 110 and the surgical procedures from which such surgical data is obtained may be located in a plurality of geographic locations. Before, during, and after a given surgical procedure for a given patient, various types of surgical data associated with such surgical procedure and such patient may be collected using various types of data sources $D_1$-$D_n$, such as shown for patient $P_1$. The surgical data may be transmitted from each data source $D_1$-$D_n$ to central computer 100, either directly or through one or more intermediate components, using any suitable type of signal or communication hardware or protocols, whether wired, wireless, or otherwise. For example, data sources $D_1$-$D_n$ may communicate signals representative of the surgical data using serial ports, parallel ports, modems, Ethernet ports, USB ports, Firewire, RS232 ports, or any other suitable types of communication ports. At a given surgical facility, one or more of the data sources $D_1$-$D_n$ may transmit surgical data to a local computer 10, which in turn transmits the surgical data to central computer 100 via a network 20. Network 20 may include but is not limited to the Internet. Among other things, central computer 100 may be programmed with one or more computer programs containing instructions for receiving input signals representative of the surgical data, storing the surgical data in central database 110, and providing access to the surgical data to a plurality of authorized users $U_1$-$U_m$ by sending one or more output signals to the authorized users $U_1$-$U_m$ in response to one or more queries, the output signals being representative of one or more portions of the surgical data. Central computer 100 may be programmed with instructions for performing one or more operations on one or more pieces of raw surgical data in order to generate one or more pieces of derived surgical data, which may be included in central database 110 and in the output signals. In this manner, a plurality of authorized users $U_1$-$U_m$, which may or may not be located at the same geographic location and may or may not be related in some respect, may realize the value of the surgical data associated with a plurality of patients $P_1$-$P_r$, some or all of whom may or may not have any relationship with a given authorized user. Central computer 100 may be programmed with instructions to allow or disallow each authorized user to have access to certain portions of the surgical data on central database 110 in order to protect the privacy of the patients $P_1$-$P_r$. For example, central computer 100 may be programmed to be compliant with certain laws and regulations, such as the Health Insurance Portability and Accountability Act.

One possible source of surgical data to be stored in the central database 110 may be one or more of the authorized users $U_r U_m$. For example, if an authorized user requests a password to be able to access the central database 110, central computer 100 may be programmed with instructions to require certain particular user registration data to be entered, such as doctor name, years of experience, specialty, medical school, primary position (private practice or hospital doctor), age, address, phone number, email address, and other information concerning the user. Some or all of this user registration data may be stored in central database 110 and automatically associated with surgical data related to that user, without the need for the user to re-enter the user registration data each time surgical data for a given surgical procedure is uploaded to central database 110. For example, whenever an authorized user logs on to central computer 100, any surgical data transmitted to central computer 100 may be tagged or identified with the authorized user's registration data in central database 110. In some embodiments, authorized users may be compensated for sending or causing surgical data to be sent to central computer 100 for inclusion in central database 110. For example, orthopedic implant companies or other medical companies could pay legitimate compensation to doctors each time the doctors contribute surgical data to central database 110.

Figure 2:
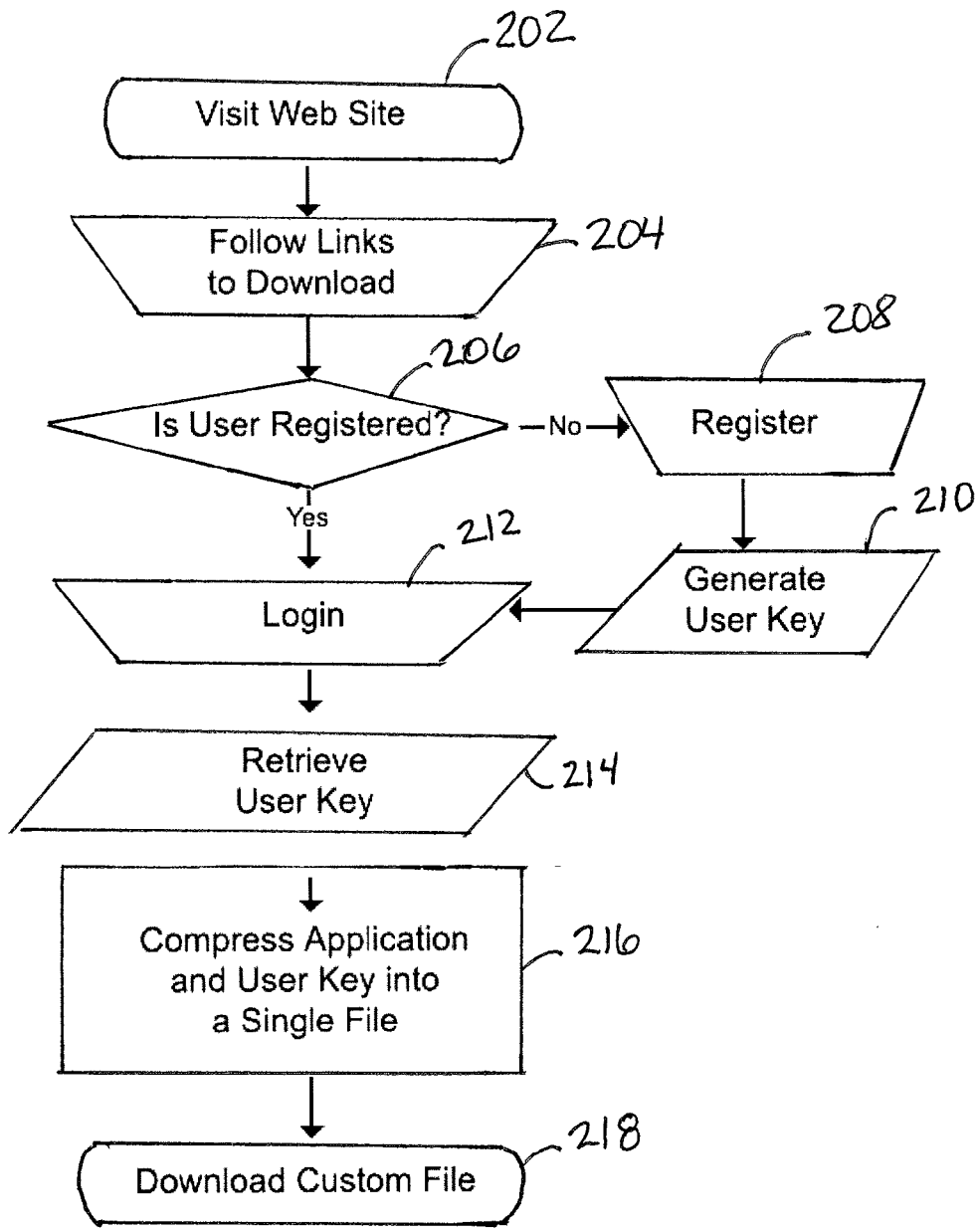
FIG. 2 is a flowchart of a registration and download process for a client computer software application.
Figure 3:
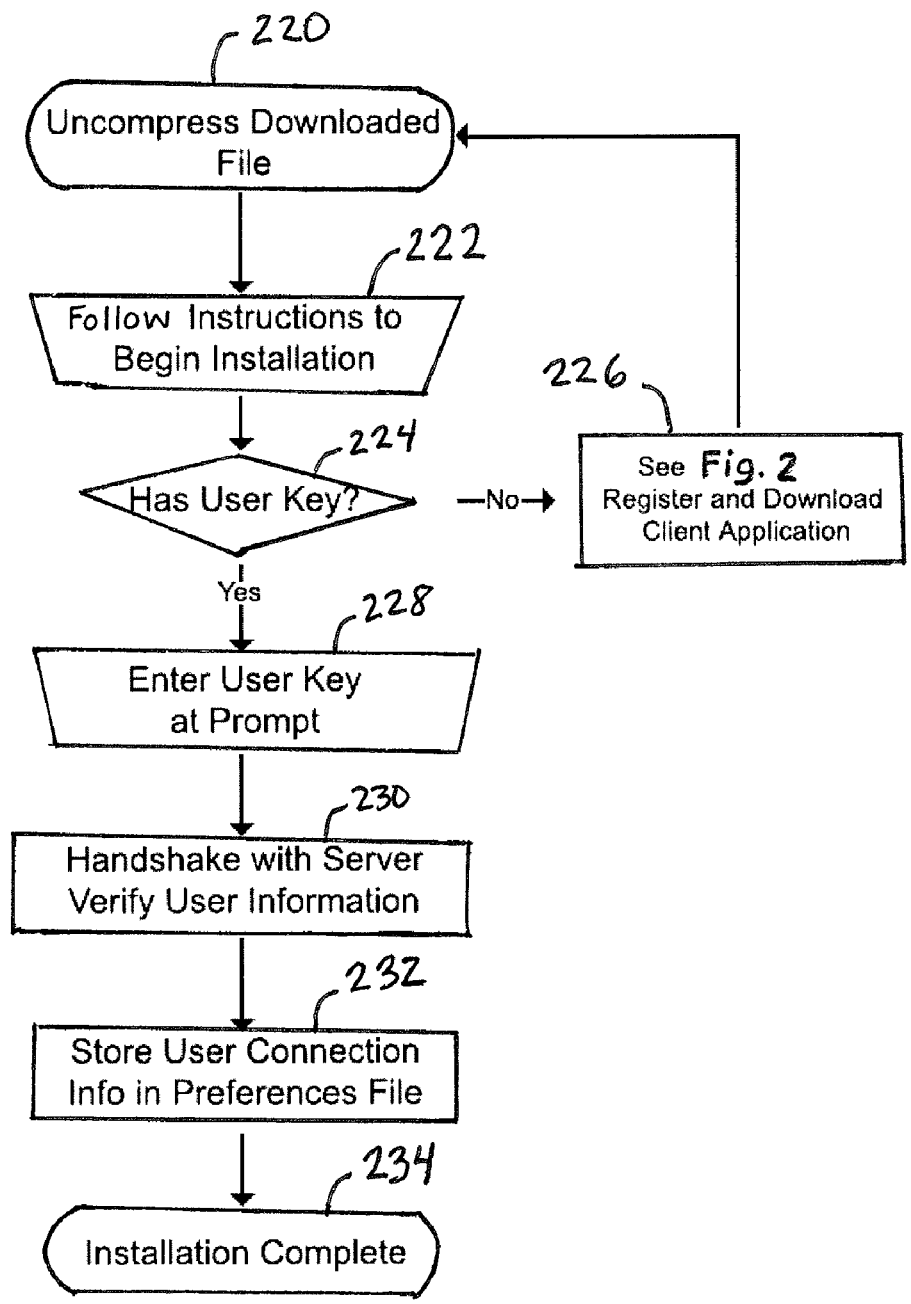
FIG. 3 is a flowchart of an installation process for a client computer software application.
Figure 4:
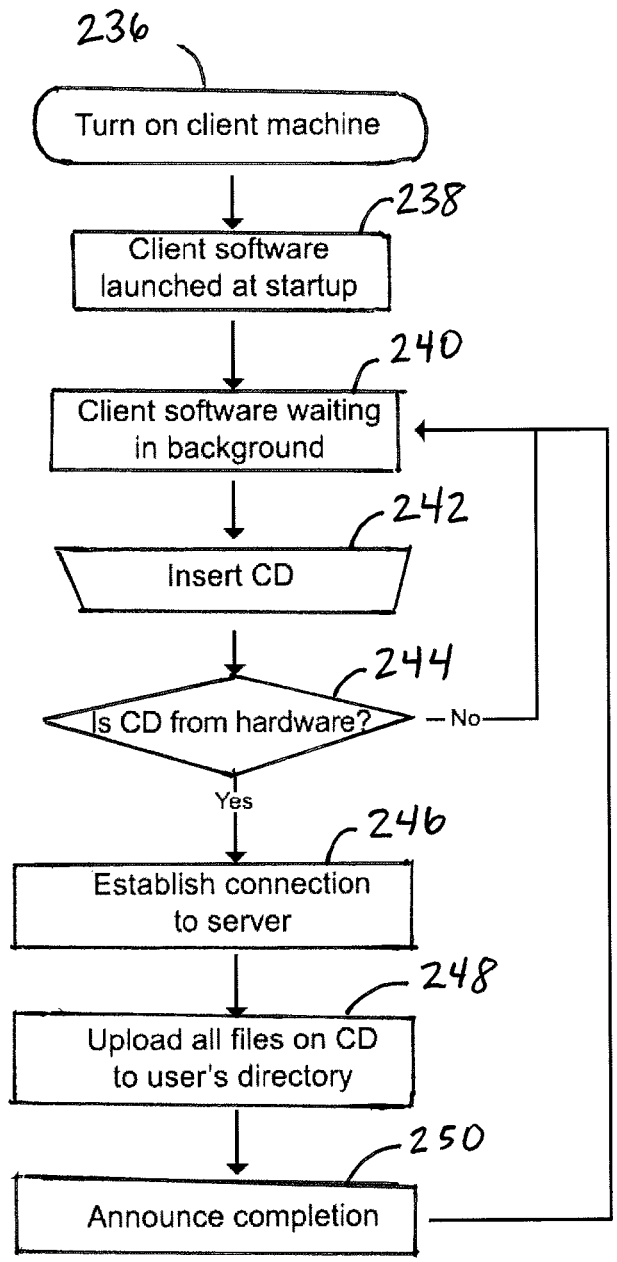
FIG. 4 is a flowchart of an upload process involving extraction of surgical data from a CD and loading the surgical data onto a central computer database.
Figure 5:
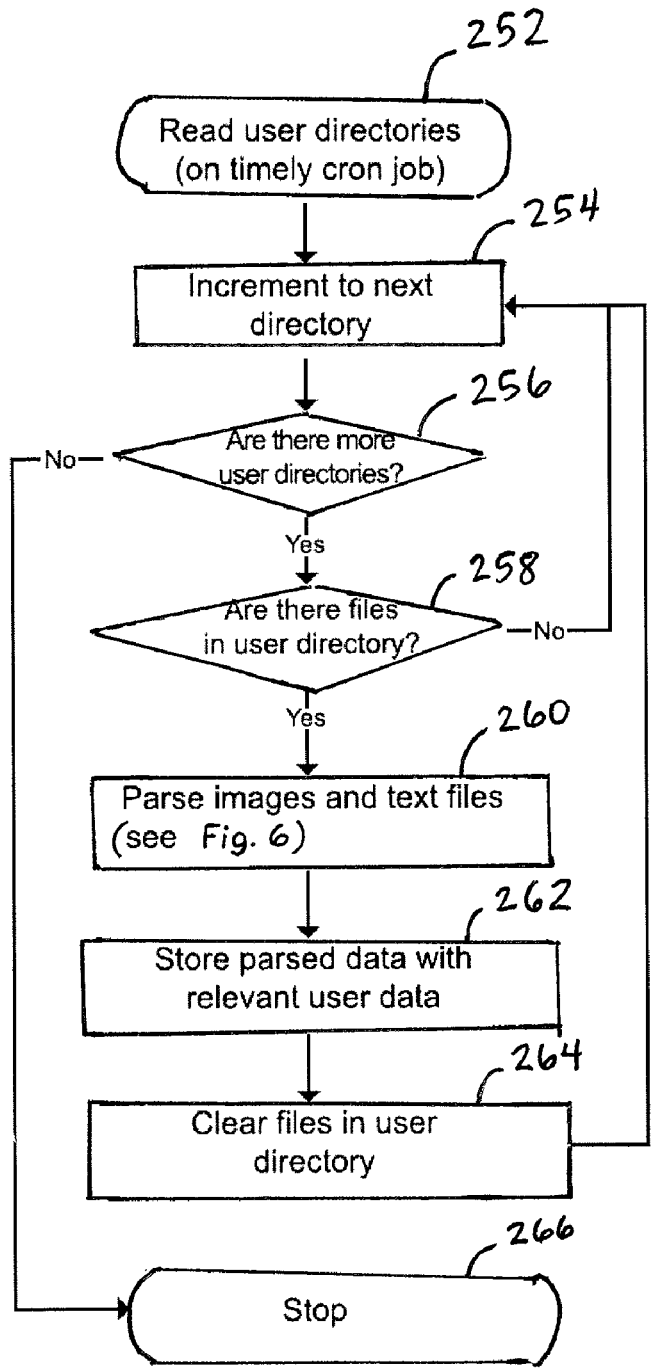
FIG. 5 is a flowchart of a user information reading process.
Figure 6:
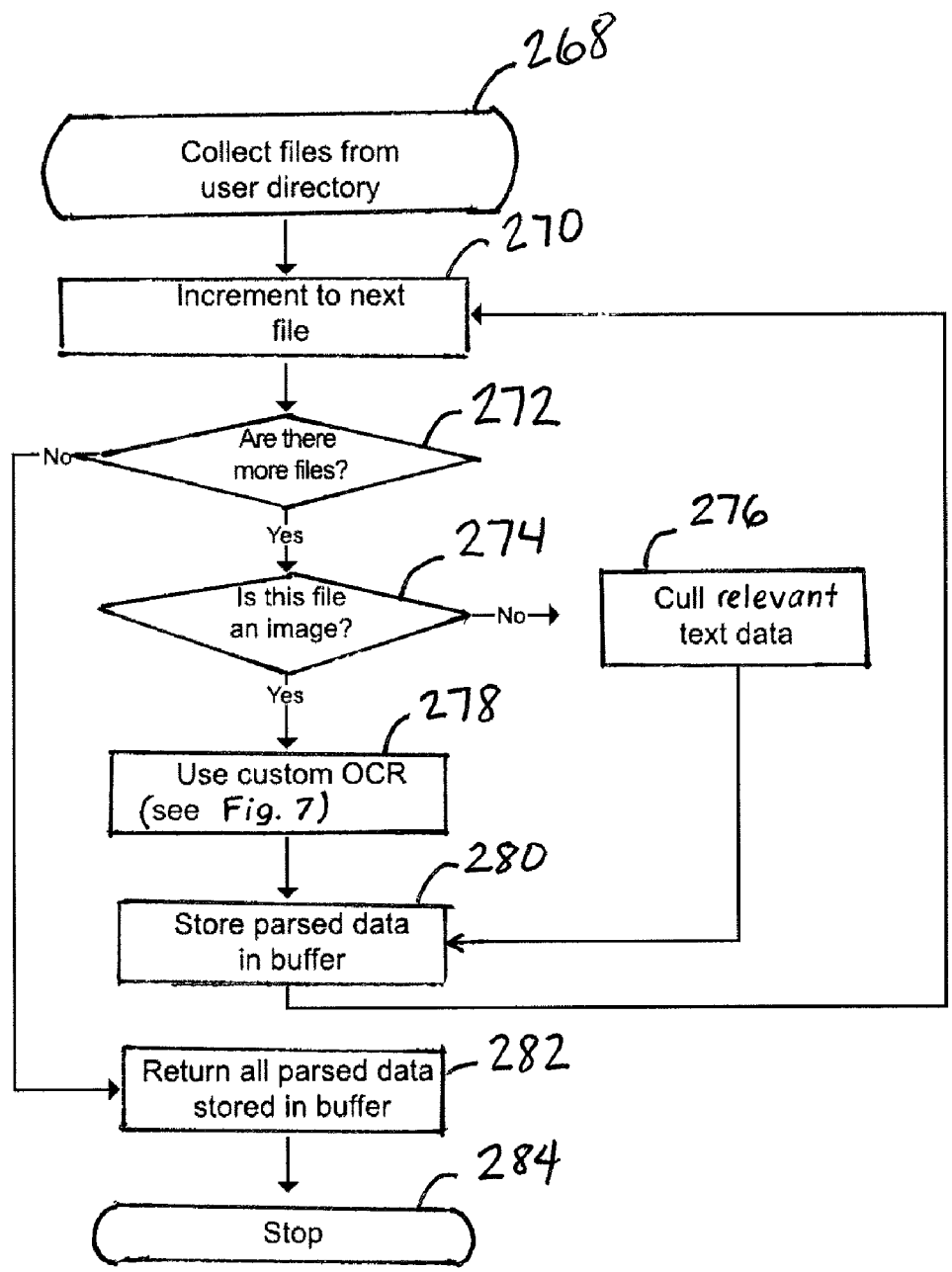
FIG. 6 is a flowchart of a surgical information parsing process.
Figure 7:
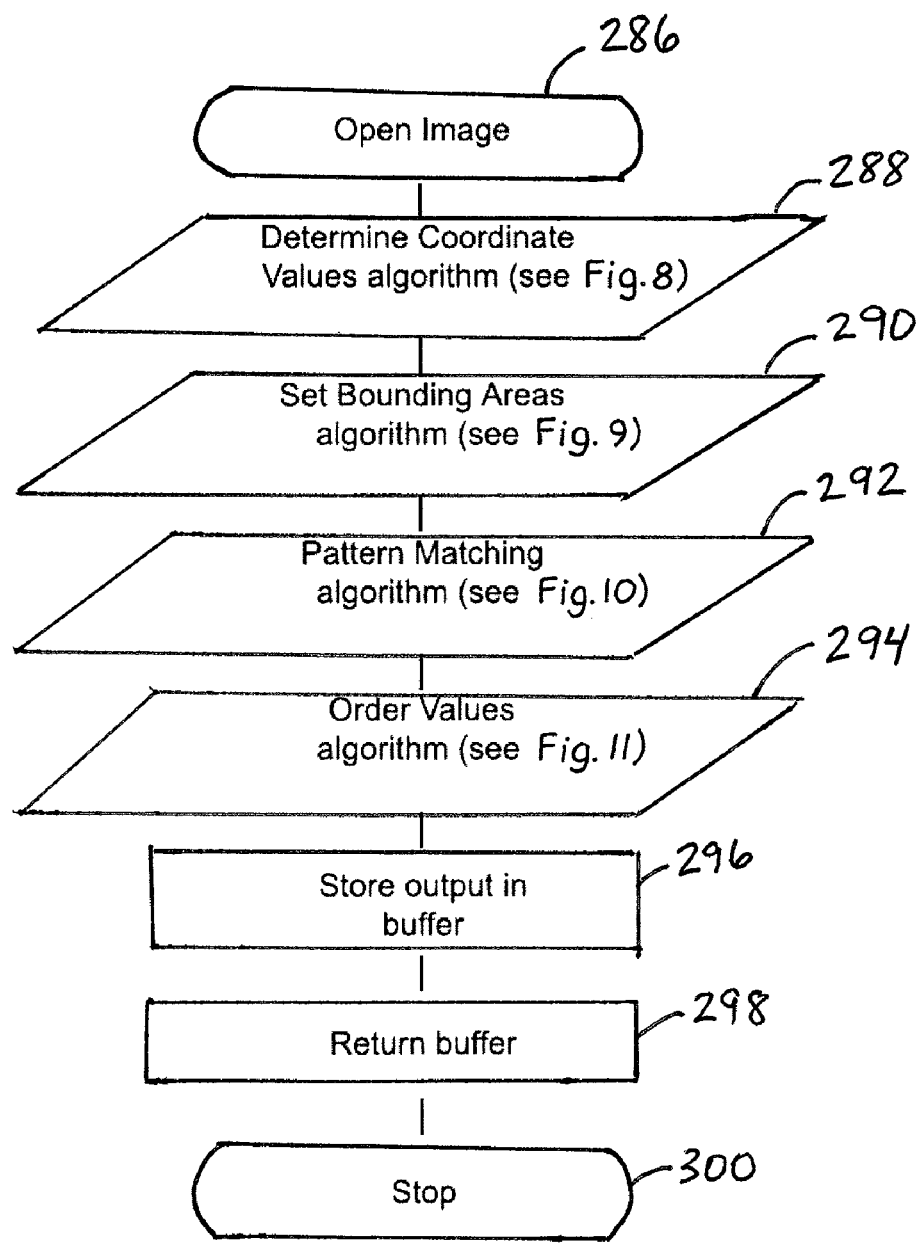
FIG. 7 is a flowchart of an optical character recognition process.
Figure 8:
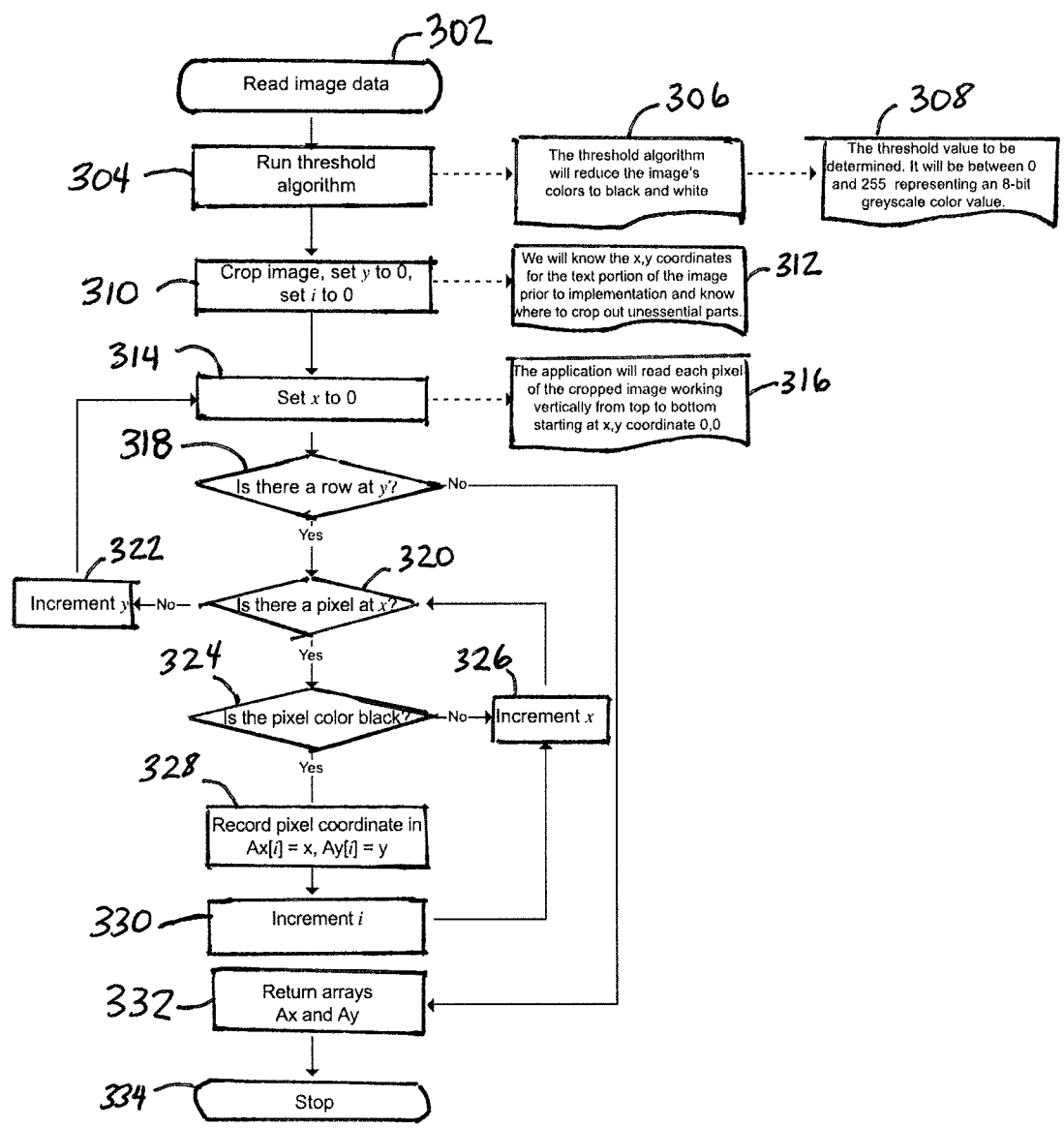
FIG. 8 is a flowchart of a portion of an optical character recognition process for determining the locations of alphanumeric text in an image.
Figure 9:
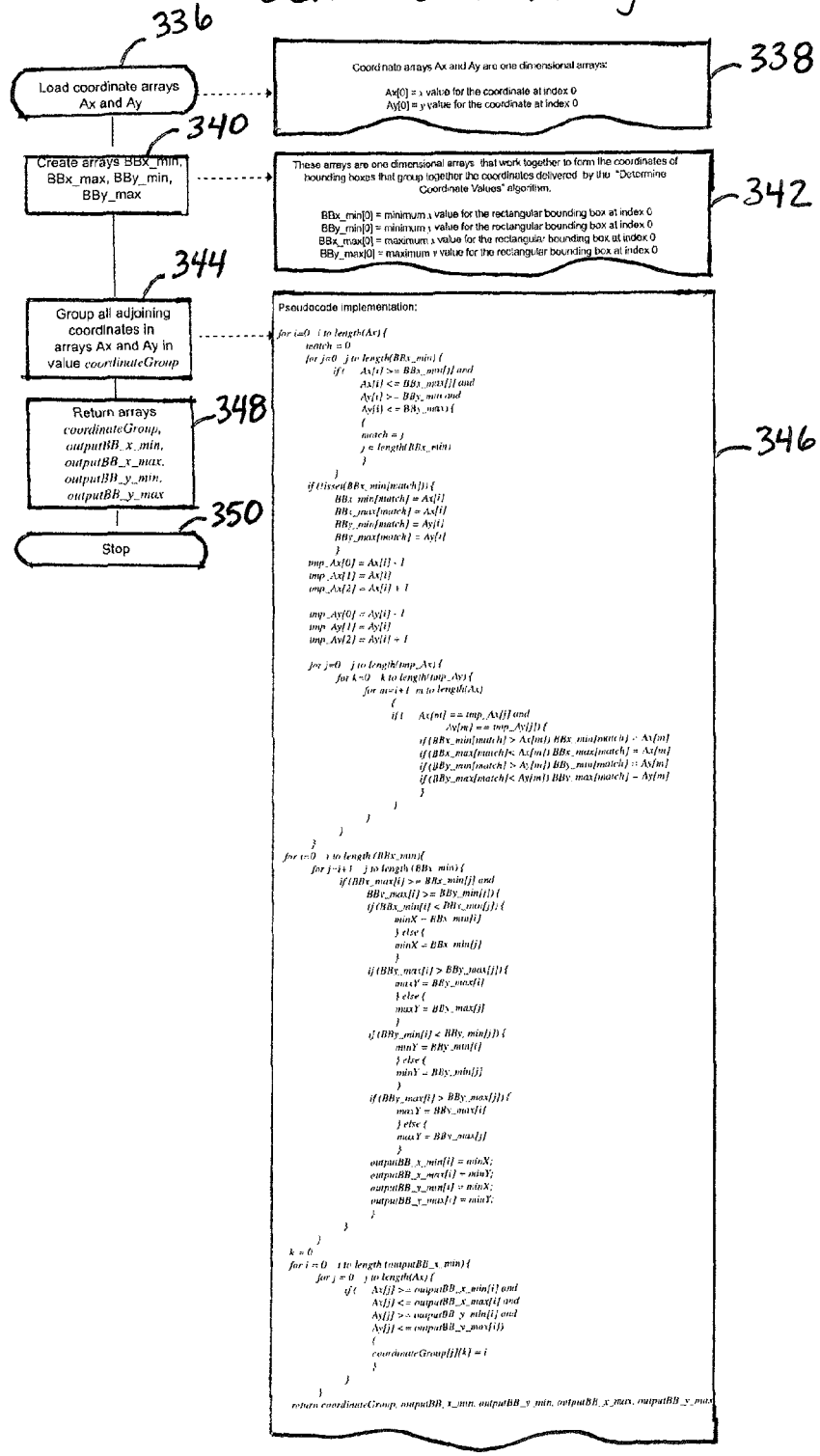
FIG. 9 is a flowchart of a portion of an optical character recognition process for establishing bounding areas for each character of alphanumeric text in an image.
Figure 10:
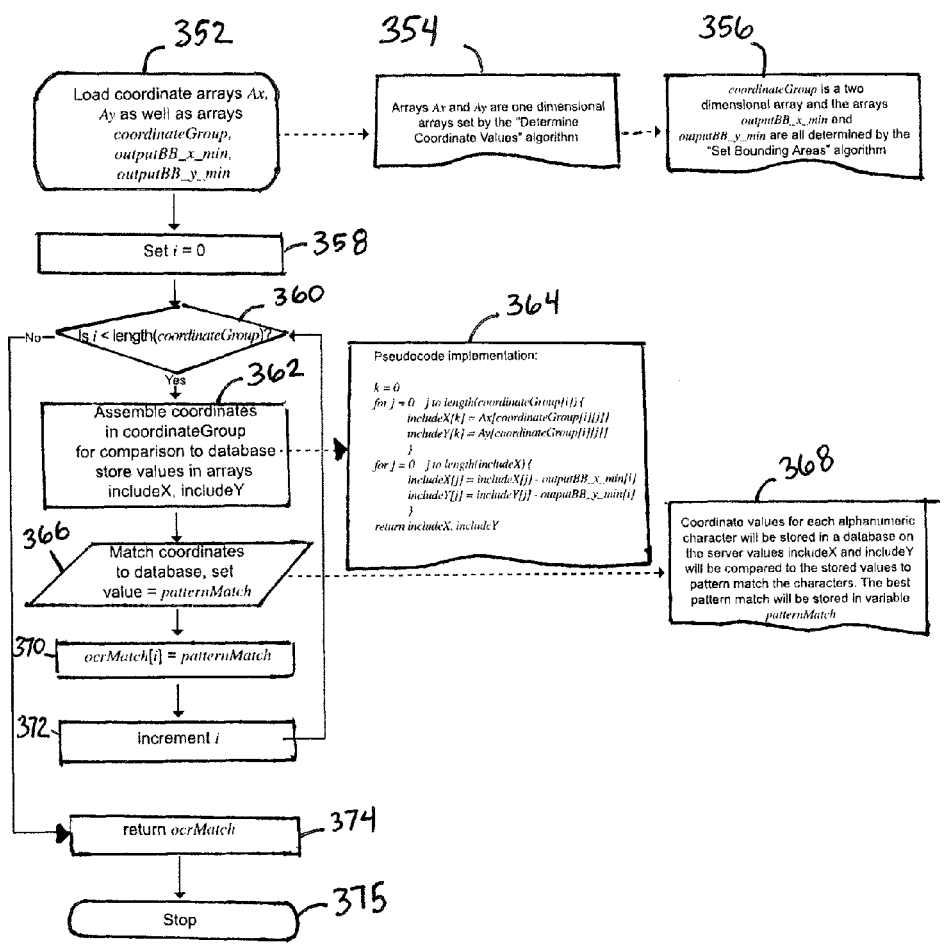
FIG. 10 is a flowchart of a portion of an optical character recognition process for matching patterns for each character of alphanumeric text in an image with known character patterns stored in a database.
Figure 11:
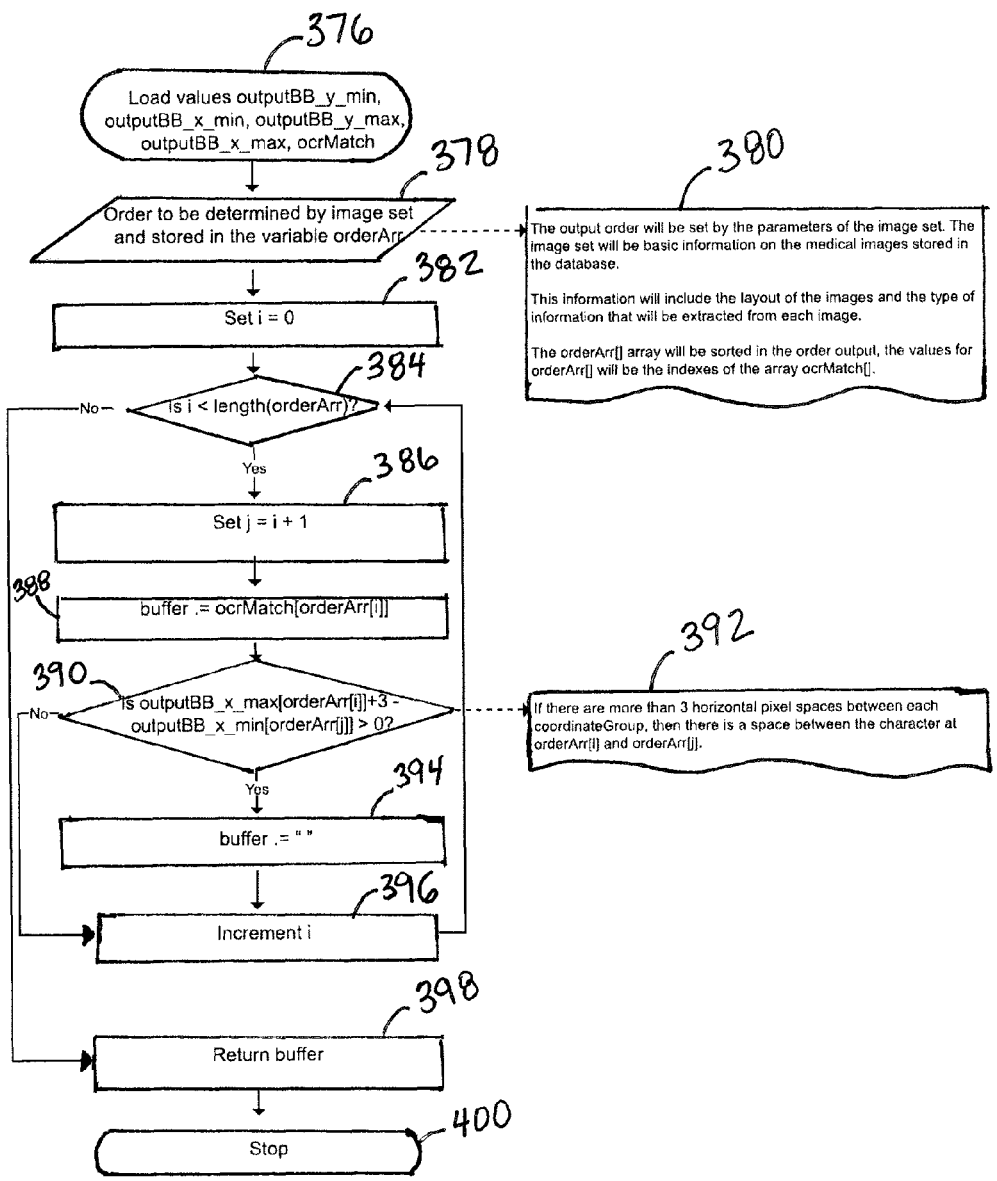
FIG. 11 is a flowchart of a portion of an optical character recognition process for ordering the characters recognized by the process.

Depending on how the central computer 100 is programmed, authorized users may need to install a client application on their local computers in order to access central database 110. FIGS. 2 and 3 illustrate one embodiment of how that may work. As shown in FIG. 2, a user may download a client application by going to a specified web site as indicated at 202 and following links to the appropriate downloadable client application as indicated at 204. The software may ask the user whether the user is registered at 206. If yes, the software may present a login screen and the user may enter his or her user ID and password code as indicated at 212. If the user is not registered, the user may be prompted to register as indicated at 208. Once registered, the software may generate a specific user key as indicated at 210, which may initiate a client login as indicated at 212. After login, the software may retrieve the user key specific to that user as indicated in 214. Of course, other ways of establishing user authorization may be used, and a client-side application may or may not be used.

Figure 31:
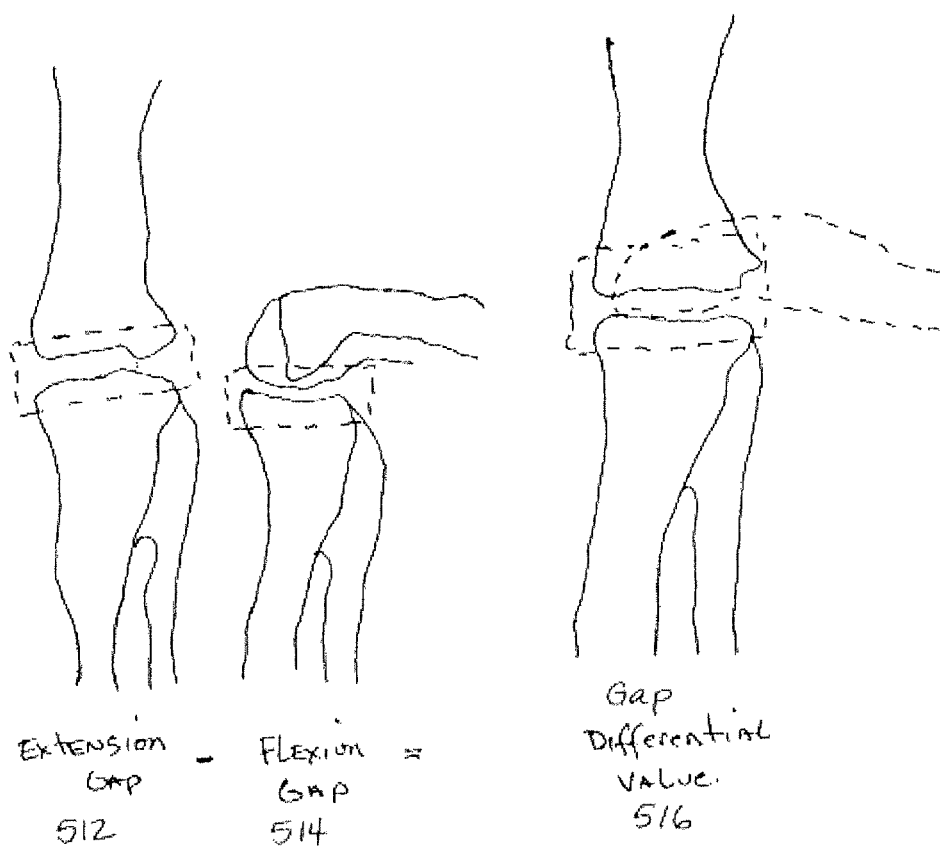
FIG. 31 is a schematic diagram showing a knee in an extension position and a flexion position to illustrate a gap differential.
Figure 32:
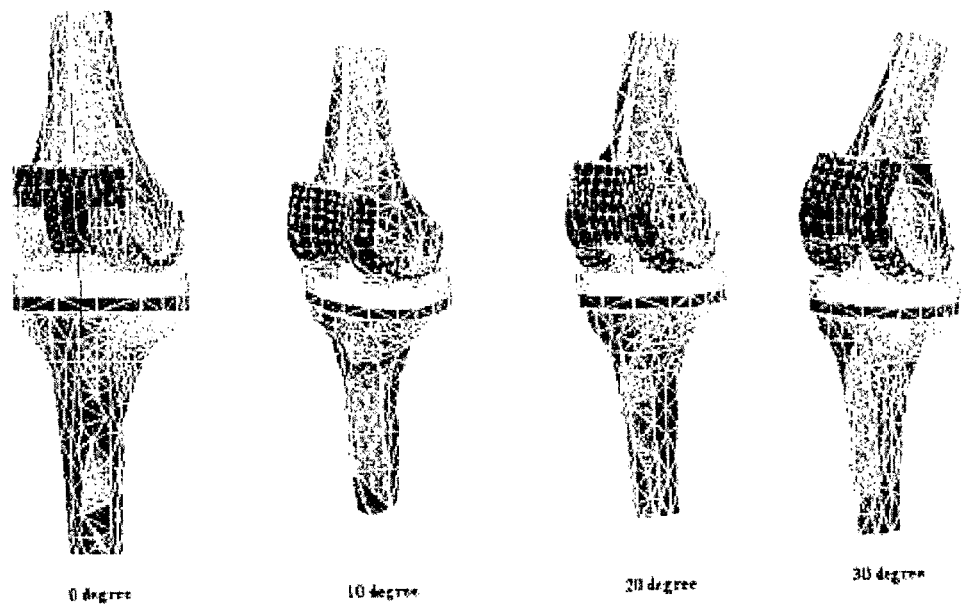
FIG. 32 is a series of computer generated models of a knee in various degrees of flexion.
Figure 38:
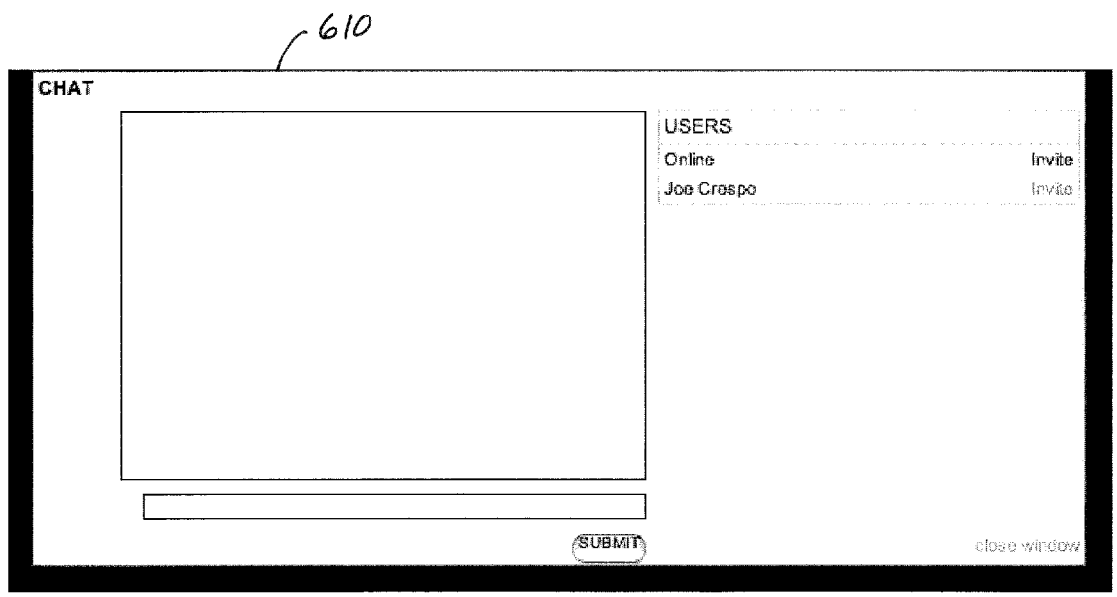
FIG. 38 is a screen shot of a sample chat window.
Figure 40:
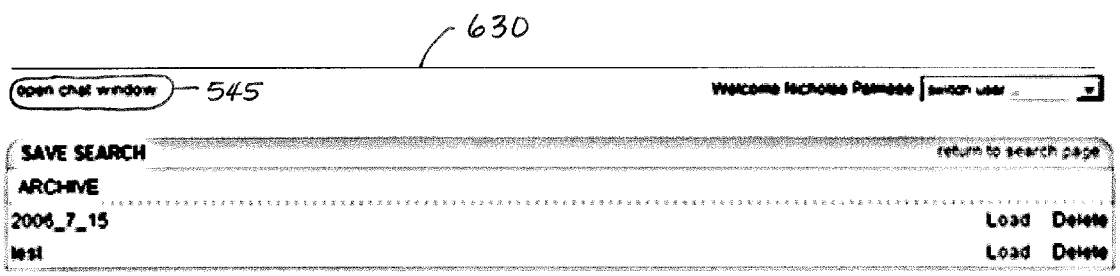
FIG. 40 is a screen shot of a sample saved search criteria window.
Figure 42:
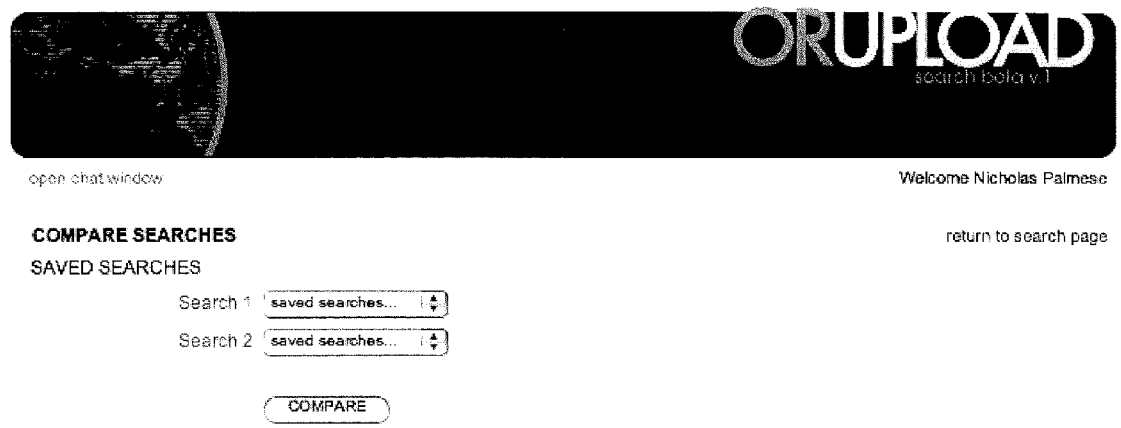
FIG. 42 is a screen shot of a sample search comparison screen.

For example, and not by way of limitation, in the context of orthopedic surgery, Table 1 illustrates some types of surgical data that may be collected and FIG. 36 illustrates a sample search screen 542 of a graphical user interface that an authorized user may use in order to perform queries of the central database 110 to obtain information regarding knee surgeries that have been performed on a plurality of patients by a plurality of orthopedic surgeons. In this example, a variety of search criteria may be specified, such as a range of extension gap 556-558, a range of flexion gap 560-562, a range of gap differential 564-566, types of mechanical alignment 568-572, treatment side 574, gender 576, a range of age 578-580, a range of height 582-584, a range of weight 586-588, an analysis type 590, types of diseases 592-594, and keywords 596 in various fields 598. FIGS. 28-32 illustrate various parts of a knee joint, such as a medial meniscus 502, and how the knee joins a femur 500, fibula 504, and tibia 506, as well as an extension gap 512, flexion gap 514, gap differential 516, and various degrees of flexion of a knee joint. In this example, gap differential 516 is an example of a type of derived data obtained from a calculation performed by central computer 100 using values for extension gap 512 and flexion gap 514, as shown in FIG. 31. An authorized user may specify various date ranges 544-550 or may set a particular date 552. A search query may be initiated by selecting a start button 604 or by any other desirable indication. An authorized user may save the search criteria using any suitable naming convention by selecting button 555. As illustrated in FIG. 40, the saved search criteria may be populated in a saved search criteria list 630 and may be edited by an authorized user. Editing features may include but are not limited to load, delete, insert, and protocol comparisons. By selecting the compare saved searches button 565, an authorized user may compare two or more saved searches from a comparison screen such as shown in FIG. 42. With protocol comparisons, an authorized user may track the differences in results from two or more searches and see the differences in certain data values, for example, in terms of plus or minus differentials, percentages, or other suitable comparative measures. A user may clear the search screen by selecting clear button 554. A user may specify a manner by which the results of a query may be sorted as indicated at 600-602. A user may open a chat window 610 (see FIG. 38) by selecting button 545 in order to communicate with other authorized users about any surgical data of interest. Although pull down boxes, text fields, and buttons are illustrated in FIG. 36 as means for specifying various search criteria, persons of ordinary skill in the art will recognize that any suitable means for specifying search criteria may be used, including but not limited to any suitable type of graphical user interface.

TABLE 1

1. Surgical case demographic information.
   a) Case number
   b) ID
   c) Surgery location
   d) Zip code
2. General Information.
   a) Date of treatment
   b) Time of treatment
   c) Operating area
   d) Treatment side
   e) Defect
   f) Surgeon
   g) Assistant
3. Patient Data
   a) Patient
   b) Patient ID
4. Registration
   a) Name of screen shot
5. Intra-Operative Planning (Implant Selection)
   a) Implant Product Line
   b) Implant Toolset
   c) Implant Component
   d) Implant System
   e) Implant Name
   f) Implant Size
6. Implant Fine-tuning
   a) Translation      Shift [mm]       Referenced to
      Resection        (value)          (name)
      Anterior         (value)          (name)
      Medial           (value)          (name)
   b) Rotation         Angle [0]        Referenced to
      Flexion          (value)          (name)
      Varus            (value)          (name)
      Internal Rotation (value)         (name)
      Epicondyle Line  (value)          (name)
7. Implant Planning                     Referenced to
   a) Posterior Slope  Angle [0]        (Implant size)
   b) Varus            Angle [0]        (Implant size)
   c) Resection Low    Shift [mm]       (Implant size)
   d) Resection High   Shift [mm]       (Implant size)
   e) Internal Rotation Angle [0]       (Implant size)
   f) Medial Shift     Shift [mm]       (Implant size)
   g) Anterior Shift   Shift [mm]       (Implant size)
8. Flexion Balancing
   a) Epi:             (value in [0])   WS: (value in [0])  Post: (value in [0])
   b) Flexion          (value in [0])
   c) Ext Space:       (value in [mm]) (Med) (Lat)
   d) Flex Space:      (value in [mm]) (Med) (Lat)
9. Final Flexion Alignment
   a) Extension Gap    (value in [mm])
   b) Flexion Gap      (value in [mm])
10. Extension Balancing
    a) Flexion         (value in [0])
    b) Valgus          (value in [0])
    c) Ext Space       (value in [mm]) (Med) (Lat)
11. Final Extension Alignment
    a) Extension Gap   (value in [mm])
    b) Valgus          (value in [0])
    Preoperative Information
    c) Valgus          (value in [0])
    d) Extension       (value in [0])
12. Distal Resection Data

|  | Current | Planned | Deviation |
|---|---|---|---|
| Varus | (value in [0]) | (value in [0]) | (value in [0]) |
| Flexion | (value in [0]) | (value in [0]) | (value in [0]) |
| Resection | (value in [min]) | (value in [mm]) | (value in [mm]) |

13. A/P Resection Data

TABLE 1-continued

|  | Current | Planned | Deviation |
|---|---|---|---|
| Internal Rotation | (value in [0]) | (value in [0]) | (value in [0]) |
| Anterior Shift | (value in [mm]) | (value in [mm]) | (value in [mm]) |

14. Tibia Resection Data

|  | Current | Planned | Deviation |
|---|---|---|---|
| Valgus | (value in [0]) | (value in [0]) | (value in [0]) |
| Posterior Slope | (value in [0]) | (value in [0]) | (value in [0]) |
| Resection | (value in [mm]) | (value in [mm]) | (value in [mm]) |

15. Averaging of values for shift [mm].
16. Averaging of values for angles [0]
17. Averaging totals for a section criteria.
18. Comparison totals from (13)
19. Deviation totals with date specific range results
20. Differential values for final alignment totals averaged from case loads Again by way of example and not by limitation, FIG. 37 illustrates a sample results screen 606 of a graphical user interface by which an authorized user may view the results of a search query of central database 110. In this example, which again is for orthopedic knee surgeries, screen 606 depicts the results of a search performed on database 110 for all instances of an extension gap in the range of zero to ten millimeters. By viewing such search results, an authorized user may glean valuable information that may be used for the benefit of many individuals and entities, including but not limited to patients, surgeons, orthopedic implant manufacturers, insurance companies, research institutions, and government agencies. For example, from the search results in FIG. 37, an authorized user may observe various statistics concerning the relevant surgeries, such as the average extension gap, the average flexion gap, the average gap differential, and the mechanical alignment. Such average values may be calculated by central computer 100 and displayed for an authorized user based on the personal results of a given physician, the overall results for all physicians in the industry, or any other desirable basis. In addition to averages, any other desirable statistical values may be calculated for each type of surgical data in database 110, such as means, medians, standard deviations, and other values. In this example, screen 606 also shows specific values for various parameters of the relevant surgeries, such as final alignment (valgus and varus), final gap differential, final flexion gap, beginning flexion angle, and beginning extension angle. In some embodiments, a hyperlink may be provided for each relevant surgery so that an authorized user may pull up further information associated with a given surgery.

Persons of ordinary skill in the art will recognize that results of queries of surgical data as described herein may be used as a basis for clinical diagnostic and therapeutic decisions. For example, and not by way of limitation, the surgical data may be used to determine whether a particular surgical procedure should be performed on a given patient, and if so, which materials and equipment should be used and how they should be used. Such clinical diagnostic and therapeutic decisions may be carried out personally by an attending physician, or they may be carried out automatically by central computer 100 based on statistical data from which best practices are derived. For example, an orthopedic surgeon may utilize certain values of the surgical data to determine placement of a knee implant. Certain values of the surgical data may relate to placement of the knee implant in spatial relation to the anatomy of the particular patient's knee, and after placement, the relative distances and angles between the implant and various portions of the anatomy of the knee. A surgeon may use these values to plan the surgery and to make decisions as to what values to use for each individual knee surgery. Historically, these decisions have been made subjectively by the attending surgeon based on that surgeon's prior experience with a certain implant, or a certain type of patient with a particular medical history, or other relevant considerations known only to the particular surgeon. By contrast, embodiments of the systems and methods described herein are able to collect these values and make them available for statistical analysis to be used not only by the attending surgeon but by other surgeons and other authorized users.

For example, before a given surgical procedure on a particular patient, a surgeon may query the central database 110 to discover the average or most successful values used by other surgeons on patients having similar characteristics as the particular patient. The surgeon would then be able to use that data to establish appropriate goal values for various parameters of the surgery at issue, such as extension gap, flexion gap, gap differential, and extension balancing, for example. These goal values would be more useful than the surgeon's subjective decision as to what those values ought to be because the goal values would be a result of an analysis of a large number of patients who were treated by a large number of different physicians, and optimized values could be established based on confirmed successful operations over a long period of time. Among other benefits, this would allow a less senior surgeon to learn from the experiences of more senior surgeons by allowing access to the senior surgeons' operational results for other patients with similar characteristics. It would also allow a surgeon to determine what values are best for a particular type of implant, as the different sizes and compositions of implants may result in a different goal value to get a good surgical result.

Figure 33:
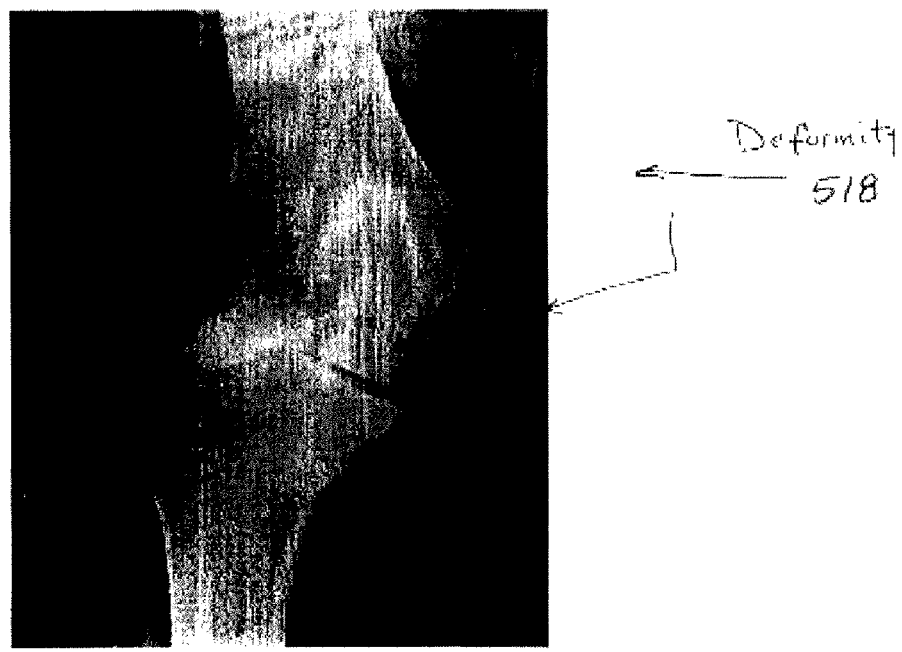
FIG. 33 is an x-ray image of a knee having a deformity.
Figure 34:
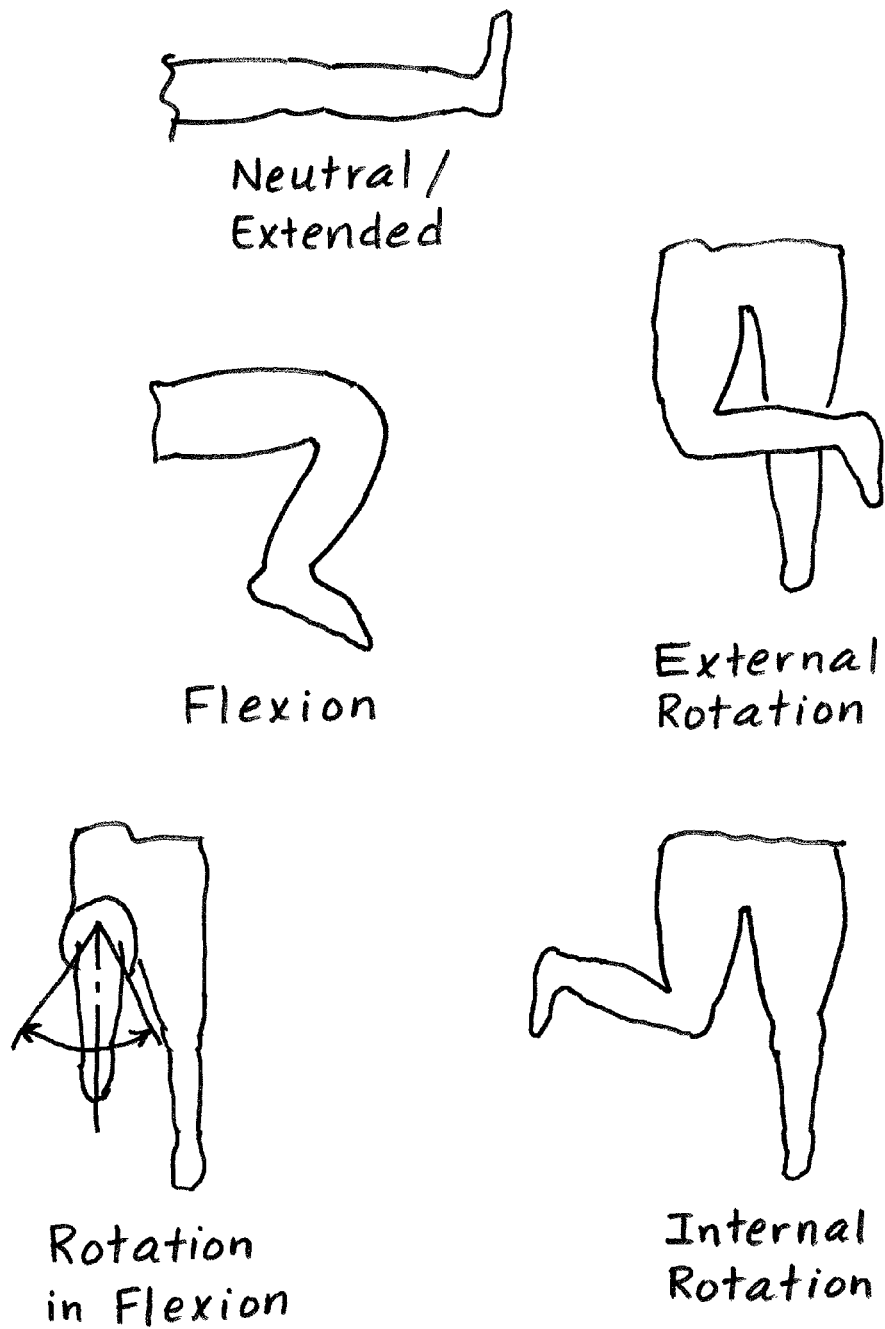
FIG. 34 is a series of schematic representations illustrating various motions of a knee joint.
Figure 35:
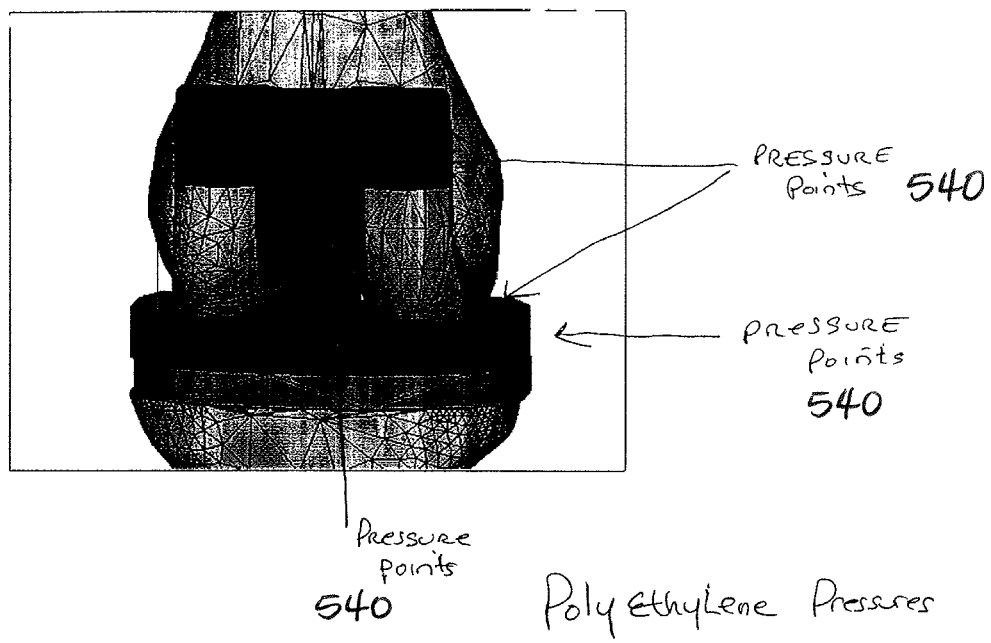
FIG. 35 is a computer generated image of a knee illustrating various pressure points.

Other examples of how such surgical data from database 110 may be used to improve the practice of surgery are illustrated in FIGS. 33-35. FIG. 33 illustrates a deformity 518 in a knee joint. By performing searches of other similar surgeries performed on patients with similar deformities and learning from the successes and failures involved, a surgeon may treat a particular deformity in a given patient in a superior manner. Surgical data from database 110 may also be used to identify optimum pressure distributions on orthopedic implant surfaces. For example, FIG. 34 illustrates various leg positions for evaluating the pressure gradients on knee implant surfaces throughout the range of motion, and FIG. 35 shows various areas of interest for achieving uniform and minimal distribution of pressure in the polyethylene material of the tibial plateau. The even distribution of a minimal amount of pressure compatible with joint stability may help to minimize wear on the joint. By performing searches on database 110 and viewing the results of other surgeries performed on other patients with the same or similar implants, a surgeon may install an implant in a given patient in an optimal manner so as to achieve a desired distribution of pressure in the joint.

Figure 13:
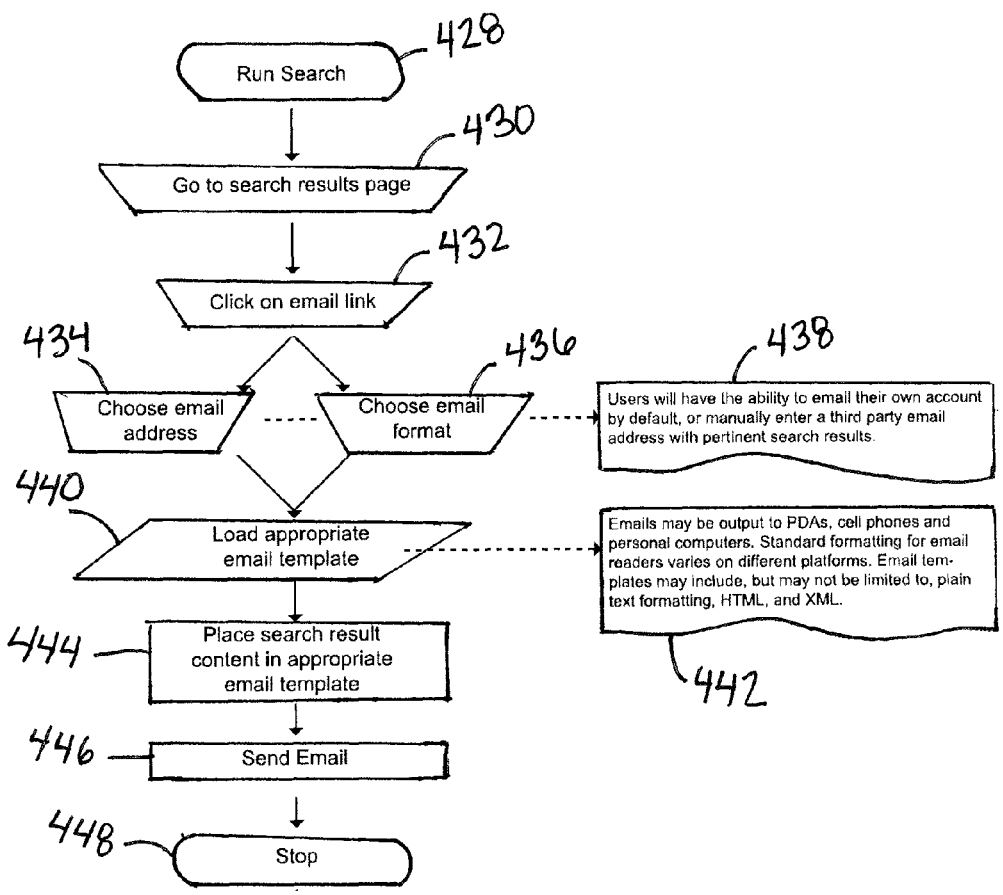
FIG. 13 is a flowchart of an electronic mail transmission process.
Figure 39:
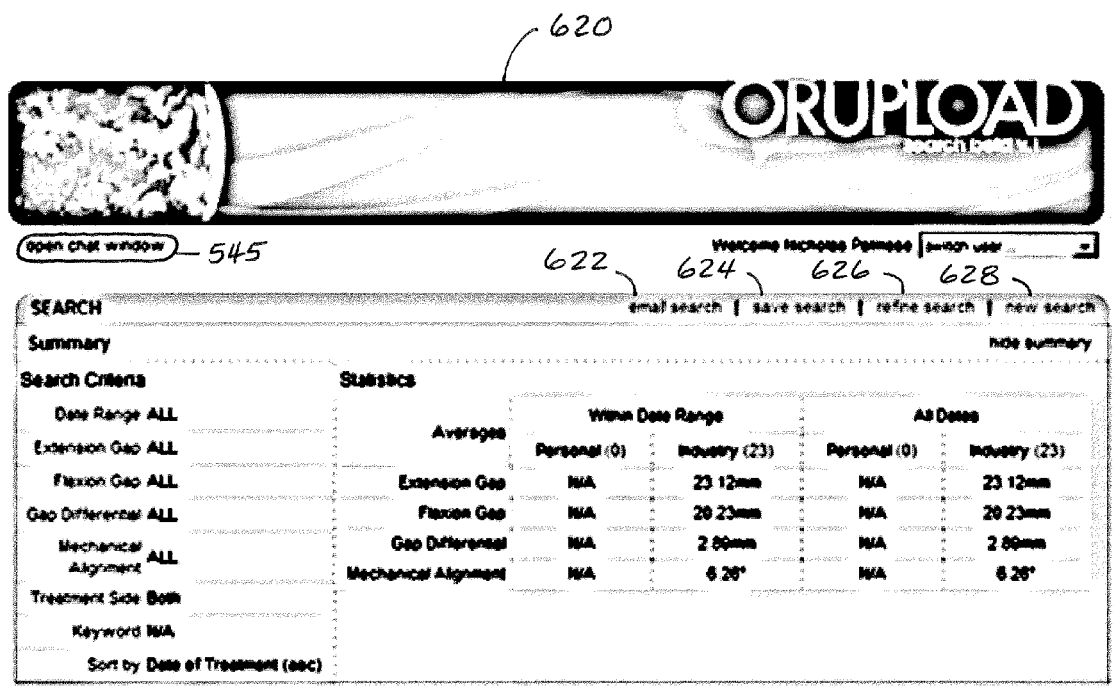
FIG. 39 is a screen shot of a sample search results summary window.

Central computer 100 may be programmed with instructions comprising a reporting module for reporting results of queries to authorized users in a variety of ways. For example, results of queries may be printed, downloaded, or displayed on a suitable display, which may be fixed or mobile. By way of example and not by limitation, an authorized user may send data resulting from certain search criteria to a designated email account, as illustrated in FIG. 13. This email account may belong to the authorized user or another designated person. As shown in FIG. 39, which depicts a summary search screen 620, the email sent may contain a summary of all the data associated with a given search in plain text or any other desired format, such as shown in FIG. 41, for example. This format may be sent to any desired device, such as a personal computer (PC), mobile PC, blackberry, personal digital assistant (PDA), or cell phone that can receive text messaging or other mobile electronic device, which an authorized user may take to any desired location. From summary search screen 620, a user may also email, save, refine, or define a new search by selecting buttons 622, 624, 626, and 628, respectively. At this point, an authorized user could also open a chat window 610 (see FIG. 38) for correspondence with other authorized users currently logged into the system by selecting button 545. The chat window 610, which could also be used for audio and video streaming, may be useful for physician training purposes. Thus, for example, a surgeon may view desired surgical data in preparation for a surgical procedure in advance while away from the surgeon's office or the operating room. Reporting of various search results may be automated based on predefined queries that may be executed periodically.

Figure 12:
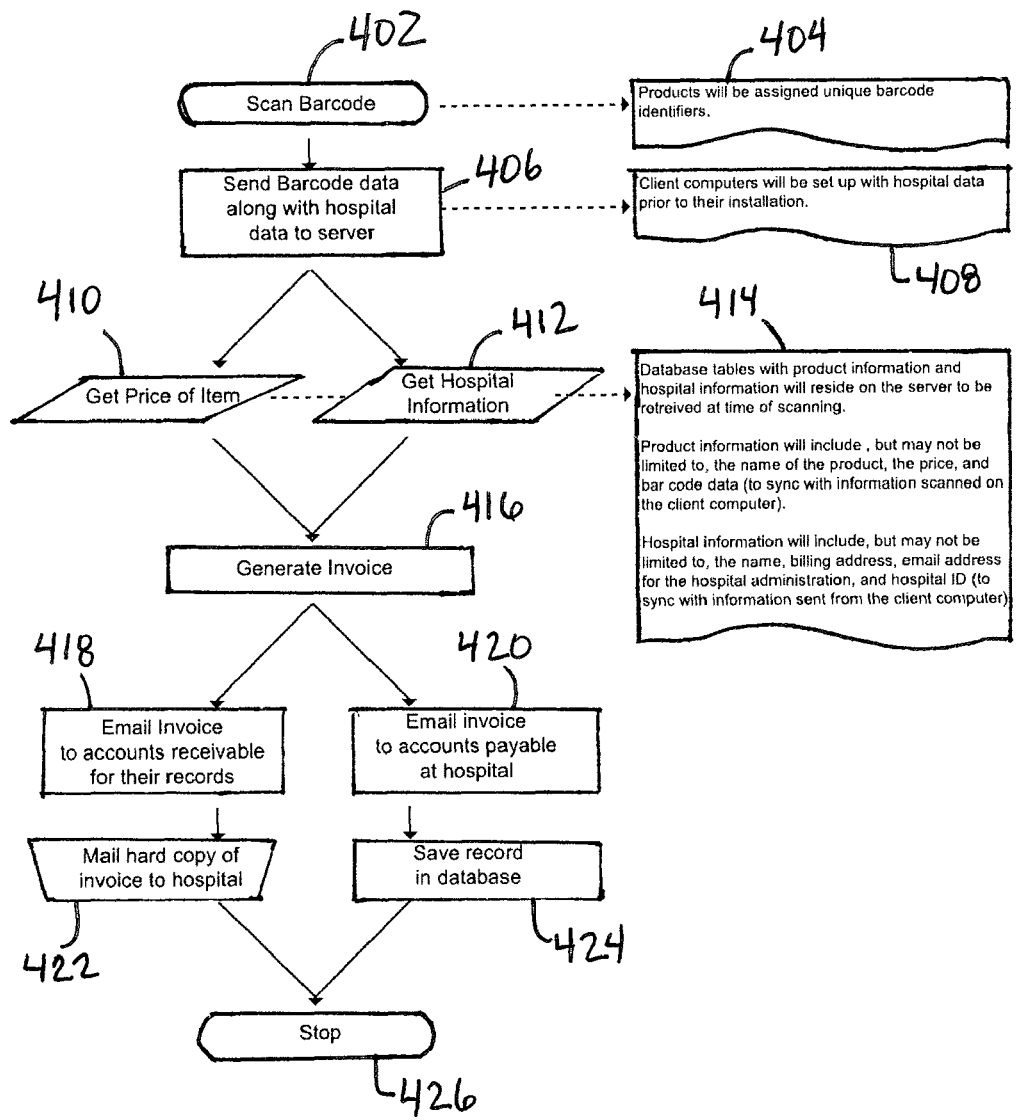
FIG. 12 is a flowchart of an inventory management process.

As mentioned above, one type of information that may be gathered during a surgical procedure is the product information of a medical implant used for a particular procedure. For example, and not by way of limitation, in connection with a knee replacement surgical procedure, all the relevant information about the replacement parts could be captured, such as product name, identification number, manufacturer, size, material, fasteners, installation tools used, and the like. This product information may be captured in any suitable manner, such as scanning with a bar code reader, reading a smart chip, or manually entering such information. The product information may be transmitted to the central computer 100 to be stored in the central database 110. Additionally or alternatively, such product information may be sent to a designated recipient, such as an implant manufacturer or hospital. The product information and other relevant surgical data may be used to generate and send an appropriate invoice to the applicable party or parties, either immediately or at a specified time. This feature enables the appropriate parties, such as physicians, hospitals, and manufacturers, to be paid sooner than is customary under presently available practices. The product information may also be used to implement a real-time or near real-time inventory process to notify the product manufacturer or other designated party that the particular product has been used. In turn, the manufacturer, hospital, or other relevant party may use that information to order or ship more products based on the knowledge of the identities and quantities of the products that have been used. An inventory management process is illustrated in FIG. 12.

In addition to the clinical diagnostic utility as described above, namely, assisting surgeons in their decisions with respect to surgical procedures, the ability of central computer 100 to perform statistical analysis on the surgical data in central database 110 could also be applied to evaluating surgeon performance, evaluating product performance, establishing surgical practitioner liability insurance, establishing patient medical insurance coverage and rates, and other applications. For example, the performance of doctors may be compared based on various statistics produced by computer 100 using the surgical data from database 110, such as the average amount of blood loss during surgery, the incidence of the need for repeat or additional surgery, or the variance of certain measurements from accepted norms, such as final extension gap, flexion gap, or gap differential. Using that information, insurance companies may make business decisions to increase or decrease the premium of a doctor or deny coverage for a doctor, depending on the level of risk indicated.

A doctor's employer could make decisions regarding training requirements based on the doctor's performance as indicated by the statistical data. A medical implant manufacturer may use those statistics to determine that a particular doctor is the most successful surgeon with the medical implant manufacturer's products and therefore hire the doctor to train other doctors on a certain implant. A medical insurance provider could utilize the surgical data made available by the database 110 to determine relative coverage of a patient group based on pre-existing conditions and risks. A surgeon could use the same information to make medical decisions on whether a particular patient group is a good candidate for a given procedure, such as knee replacement surgery, or predict likely outcomes of such surgery. Finally, a medical implant manufacturer could make marketing and business decisions by utilizing the database 110 to determine the success of its implants as compared to a competitor's implant and as compared to the average value between all medical implants 308. Medical implant manufacturers would also have just in time (JIT) inventory figures for faster clearing and accounting of implant devices and accessories that are placed in hospital operating rooms and not yet paid for. This advantage would not only give the manufacturers faster clearing and accounting for faster payment but also the ability to bring new implant designs and improvements to the market faster.

Optical Character Recognition

In one embodiment, as illustrated in FIGS. 4-11 and 14-27, an optical character recognition process may be used to collect surgical data from electronic images that have been generated by certain equipment, such as computer assisted surgical systems, and stored on any of a number of types of media, such as CDs or DVDs, for example, as follows:

Step 1: Open Image File. Load image file as a resource into memory. Deliver image resource to image editing and text recognition object.

Figure 14:
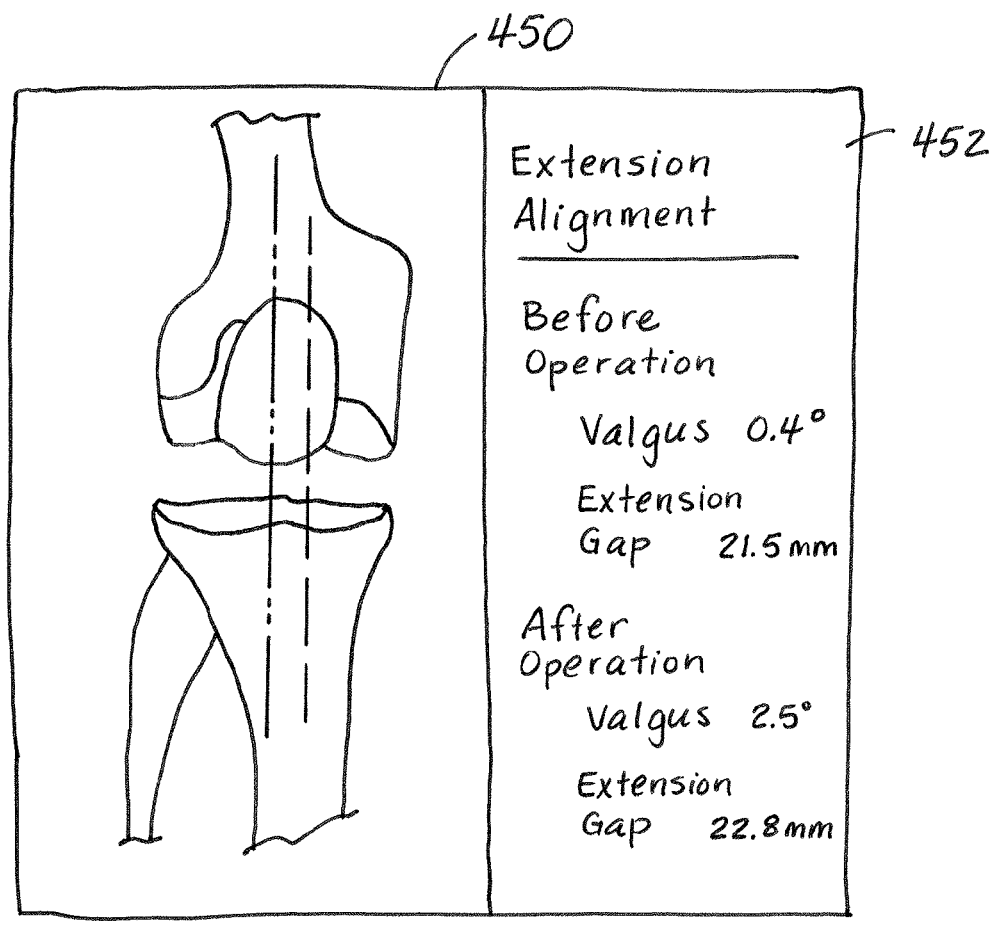
FIG. 14 is a schematic diagram of an image of a knee containing surgical data associated with the knee.
Figure 15:
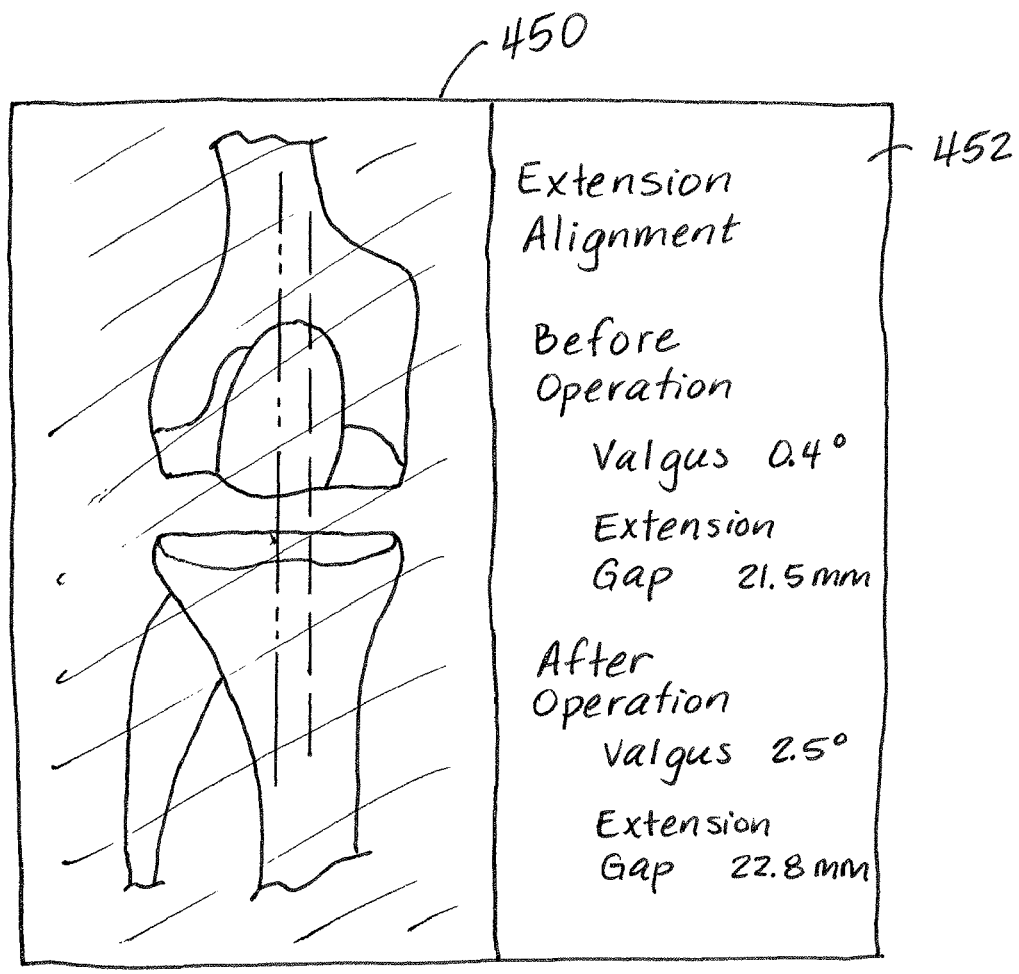
FIG. 15 is another view of the schematic diagram of FIG. 14 with a portion of interest highlighted.
Figure 16:
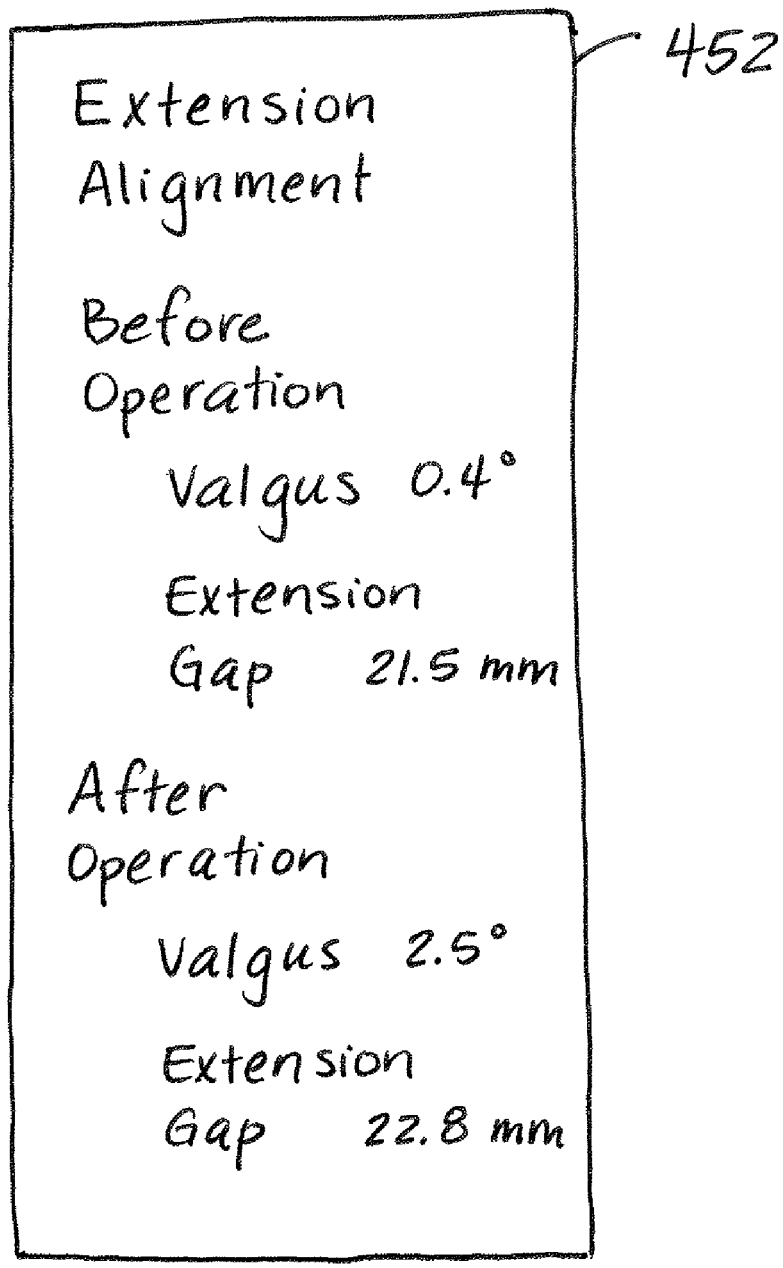
FIG. 16 is a schematic diagram of the highlighted portion of FIG. 15.

Step 2: Crop Image. There are potentially at least two areas of interest on the original images, namely, graphics area 450 and text area 452 as shown in FIGS. 14-16. These areas may be pre-defined and the crop coordinates may be coded into the object. For the purposes of this illustration, we will use the text area 452 of interest at the right of this example.

Step 3: Run Threshold Filter. The threshold filter ignores color information, essentially treating the image as grayscale, and it takes areas of light grey and makes them white and areas of dark grey and makes them black, bringing the image down to duotone.

Step 4: Bound Rows. Working along the Y-axis (vertically from the top to the bottom) of the image, each pixel along the X-axis (horizontally) is sampled. White pixels are ignored, but if a black pixel is encountered, the Y value is saved as the top of a new row. When the application encounters an entire row of white, the Y value is saved as the end of that row. This process is repeated along the Y-axis until the bottom of the image is reached and all rows are delineated as shown in FIG. 17.

Figure 18:
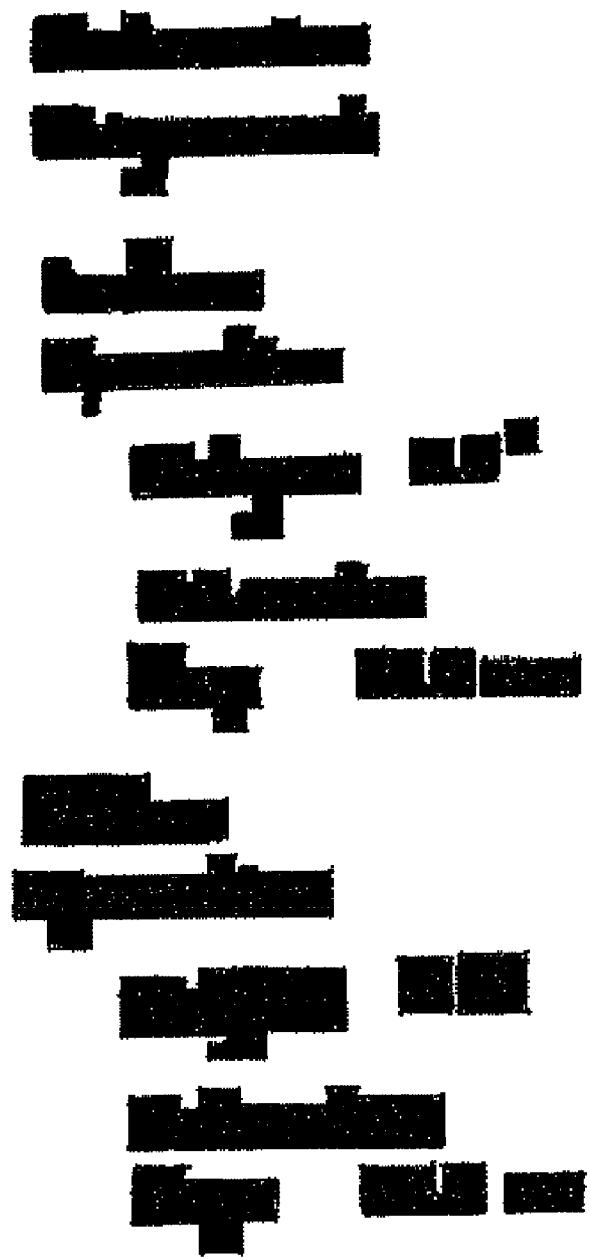
FIG. 18 is a schematic diagram of the highlighted portion of FIG. 15 with blurred text groups.

Step 5: Blur Image. Once rows are established, the image is then temporarily blurred horizontally. This is done so all letters and words that are grouped together become fused as shown in FIG. 18.

Figure 19:
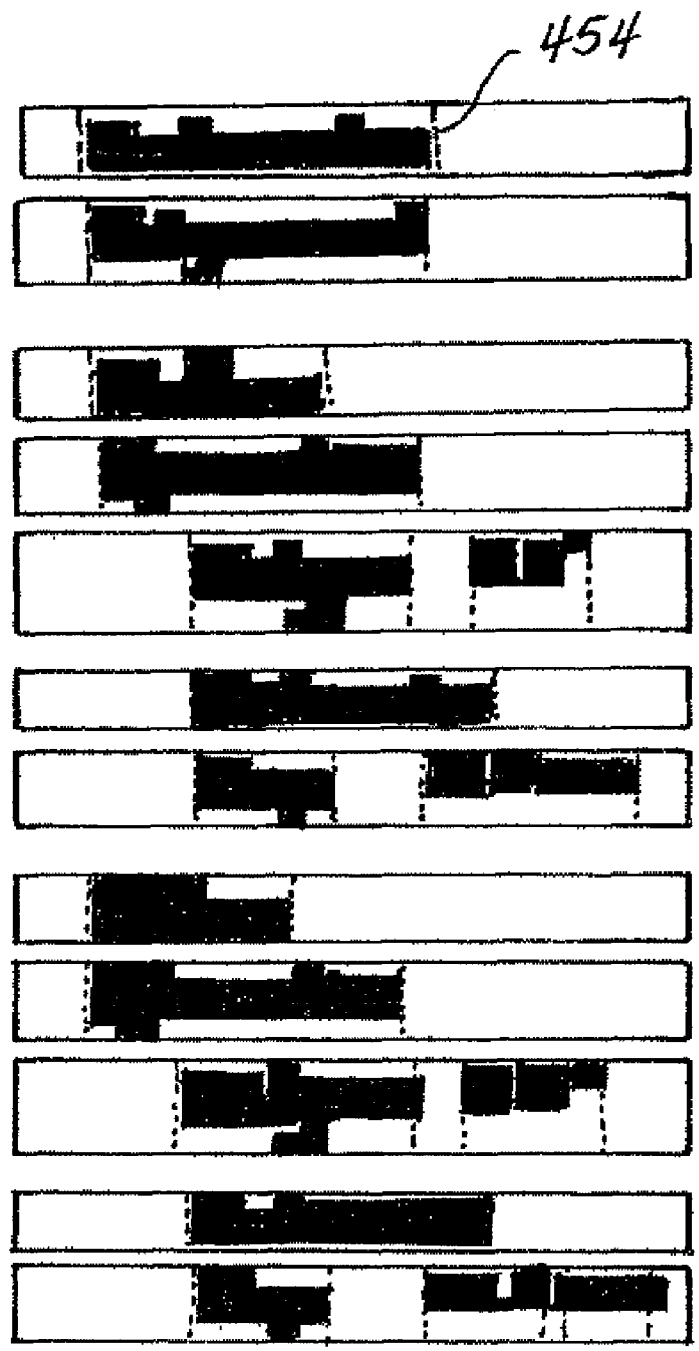
FIG. 19 is a schematic diagram of the highlighted portion of FIG. 15 showing bounded areas for the blurred text groups.

Step 6: Bound Areas. As shown in FIG. 19, taking each row in turn, the application works along the X-axis (horizontally from left to right) sampling each pixel along the Y-axis (top to bottom). White pixels are ignored, but if a black pixel is encountered, the X value is saved as the left side of a new area 454; the top of the current row is saved as the top of the current area. When the application encounters an entire vertical column of white, the X value is saved as right side of an area and the bottom of the current row is saved as the bottom of the area. This process is repeated until the application reaches the end of the X-axis, then the application moves to the next row and begins this process again and again until the final row at the bottom of the image is completed. In this example, the resulting text areas are denoted by dotted vertical lines.

Step 7: Analyze Areas. The original pixel data for each area is in turn fed back into the application. Steps 1-6 are repeated for each area. In the event that the area in question has multiple rows, this process is repeated recursively until the area being examined has a single row contained within it as shown in FIG. 20.

Step 8: Isolate letters. Once the application has boiled each area down to a single row, the threshold filter (detailed step 3 above) is run, as is the bound areas function (detail step 6 above). Each letter is now it's own area as shown in FIG. 21. The following steps are repeated for each letter.

Step 9: Set to a uniform size. Each letter is then set to a uniform size for interpretation (20 pixels wide by 20 pixels high, for example). The appropriate size of the letter may be determined by a mathematical algorithm which takes into account whether or not the area in question has lowercase letters that pierce the bottom of a line (for example, p's and q's). The original pixel data for the letter is then appropriately resized—and resampled—and copied onto a 20×20 image. The threshold filter (Step 3 above) is run on the letter.

Step 10: Create X-Axis Histogram. The application uses statistical analysis to compare images to its database of alphanumeric characters. The X-axis histogram 468 is created by ignoring Y-axis information for the image. This is done by moving along the X-axis from left to right counting the number of black pixels in each column, as shown in FIG. 22 for the letter B (indicated by reference number 466). This image as shown in FIG. 22 is created solely for the purposes of visualization of the histogram concept; it is not required in practice.

Step 11: Create Y-Axis Histogram. The Y-axis histogram 470 is created by ignoring X-axis information for the image. This is done by moving along the Y-axis from top to bottom counting the number of black pixels in each row, as shown in FIG. 23 for the letter B (indicated by reference number 466). Once again, this image as shown in FIG. 23 is created solely for the purposes of visualization of the histogram concept; it is not required in practice.

Figure 24:
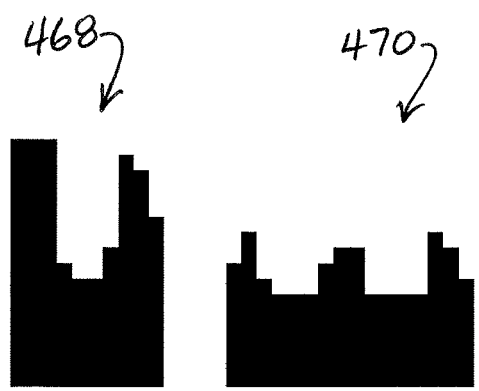
FIG. 24 is a schematic diagram of a combined histogram comprising the X-axis and Y-axis histograms of FIGS. 22 and 23.
Figure 25:
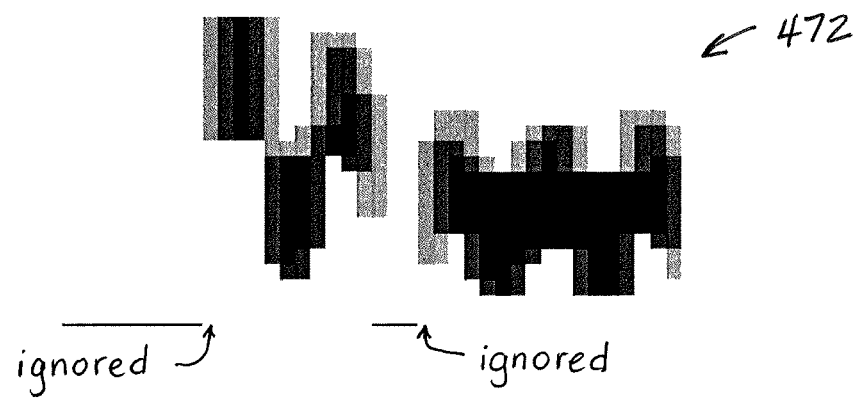
FIG. 25 is a schematic diagram of a comparison of the combined histogram of FIG. 24 to a histogram of a known character.
Figure 26:
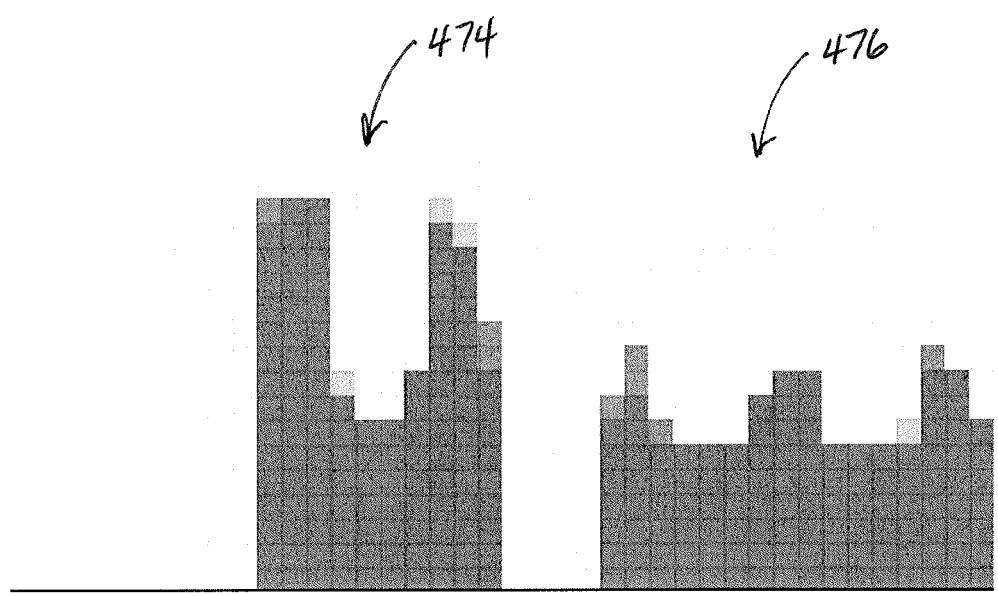
FIG. 26 is a schematic diagram of a pattern matching process for the combined histogram of FIG. 24.
Figure 27:
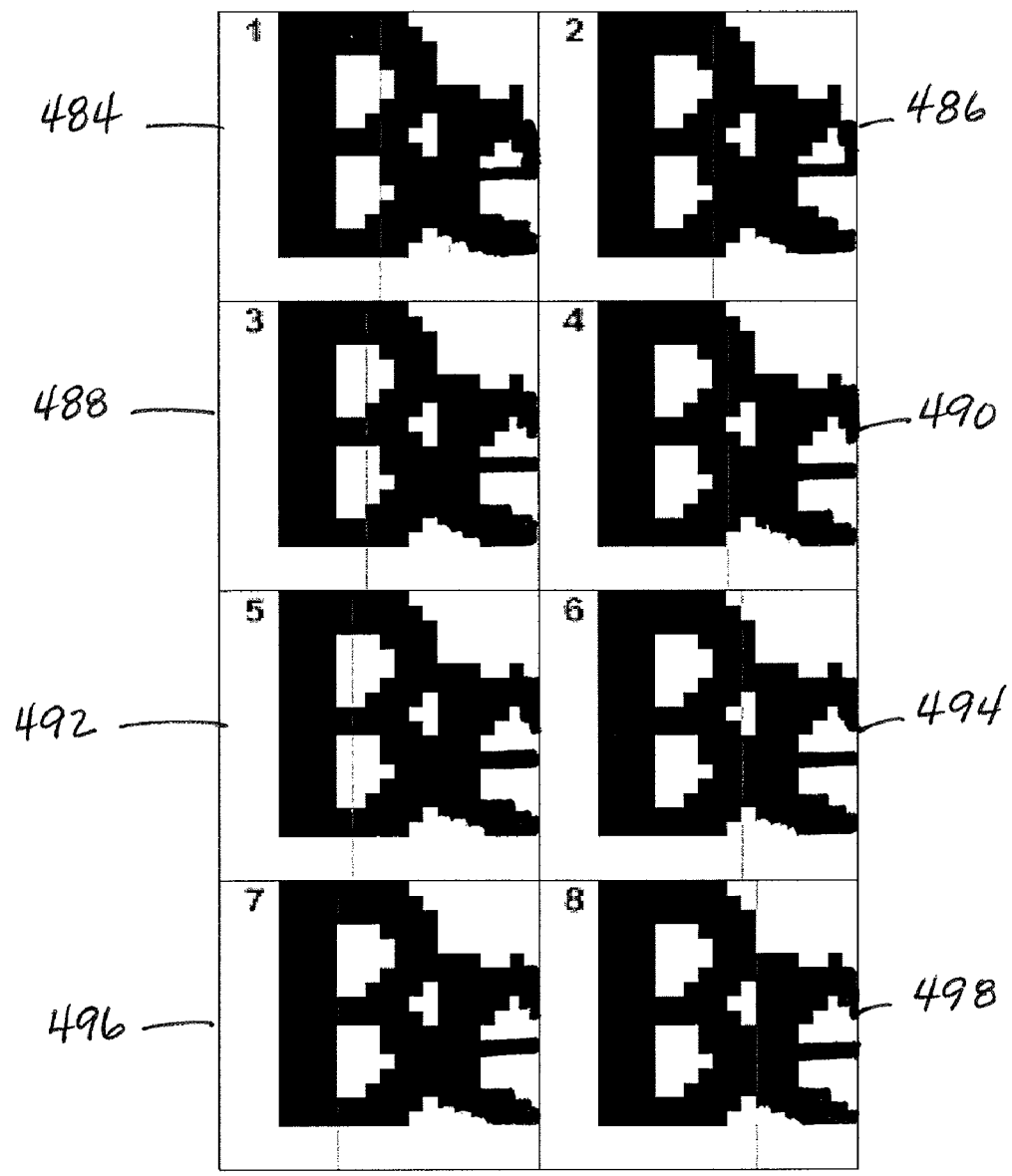
FIG. 27 is a schematic diagram of a splitting process for the first and second characters of the text of FIG. 21.
Figure 28:
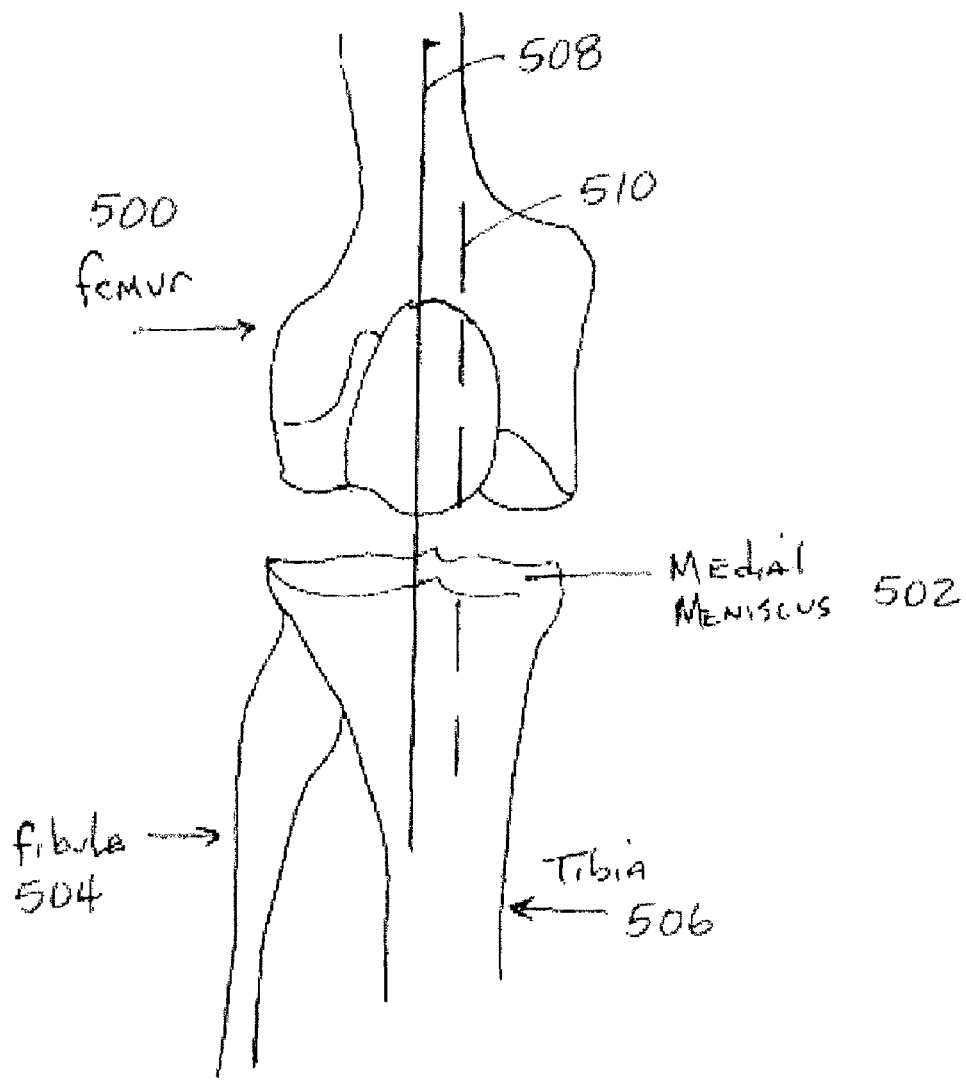
FIG. 28 is an anterior elevational view of a right knee joint in an extension position.
Figure 29:
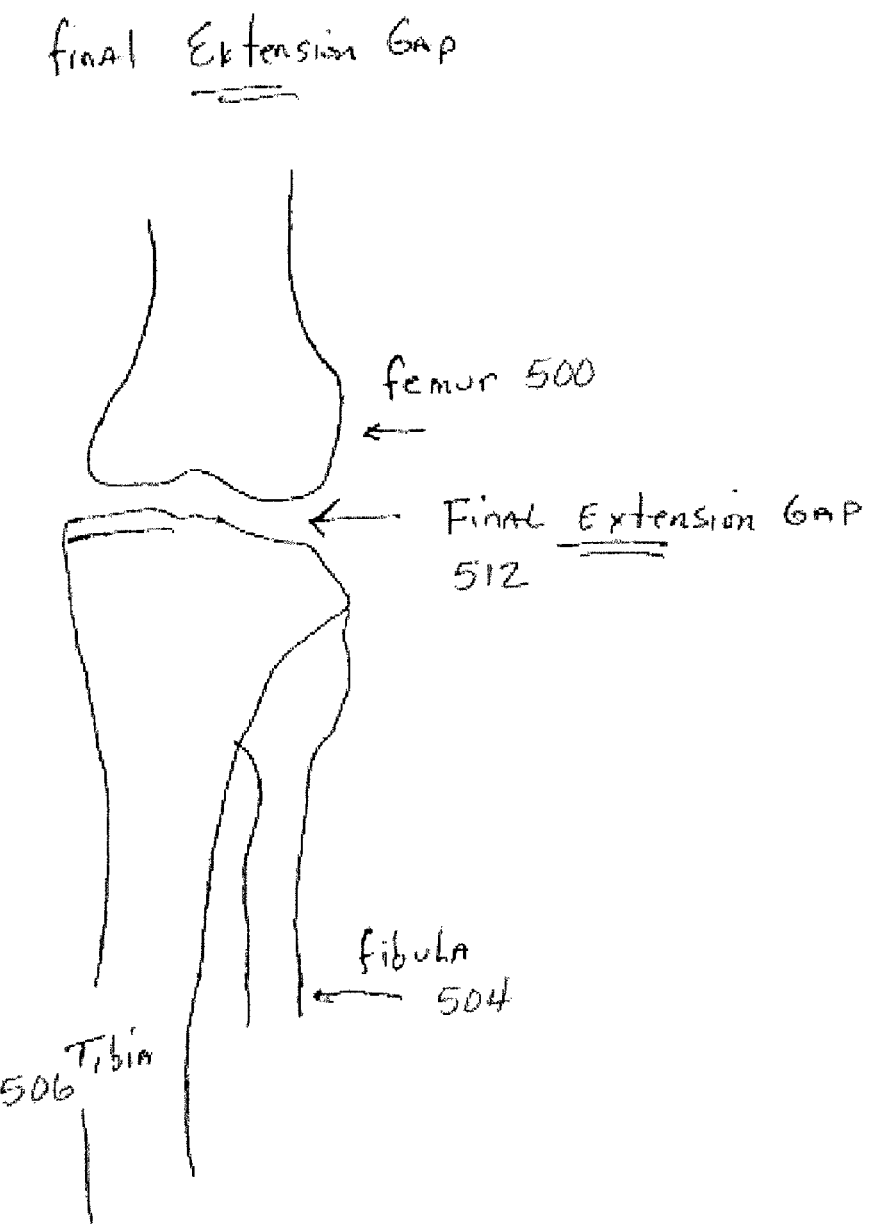
FIG. 29 is a posterior elevational view of the knee joint of FIG. 28.
Figure 30:
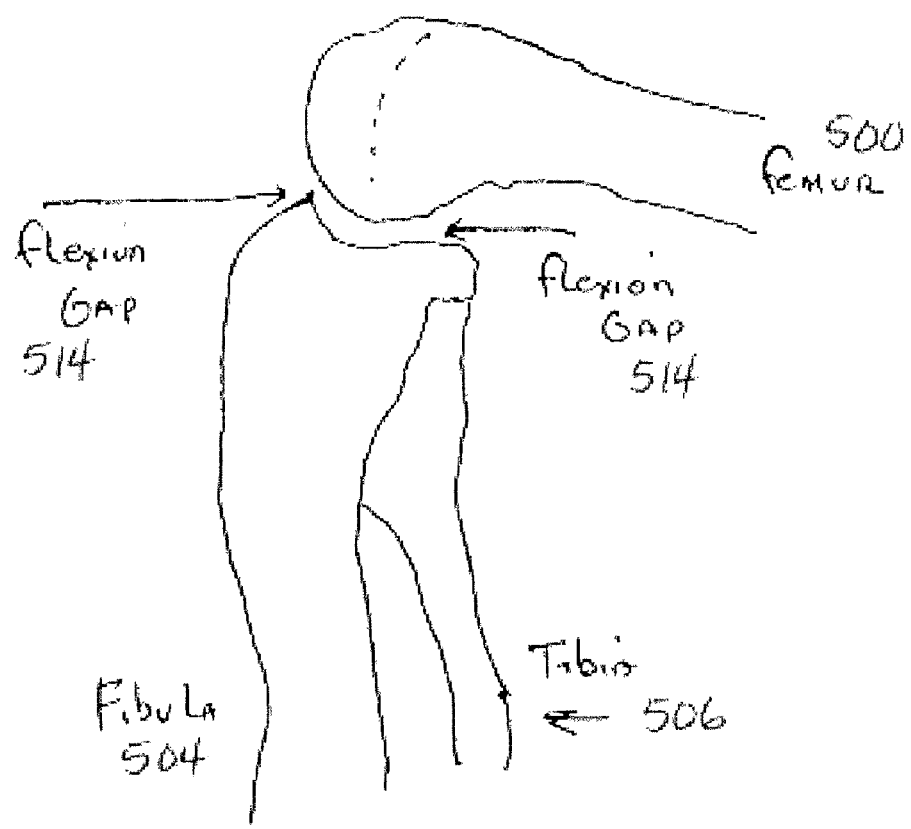
FIG. 30 is a medial elevational view of the knee joint of FIG. 28 in a flexion position.

Step 12: Combine Histograms. The two histograms 468 and 470 (X-axis and Y-axis) are combined into a 40-dimensional array (based on the 20×20 image size selected) as shown in FIG. 24. Of course, other dimensions could be used, depending on the desired degree of resolution. Again, this image is created solely for the purposes of visualization.

Step 13: Compare to Database. The application's database (housed in MySQL or another suitable database application, for example) is queried looking for any approved entries that resemble the 40-dimensional array (see more information on approving database entries in Step 16 below). A 4-pixel margin may be added and subtracted to each column of the histogram that contains values and each column may be shifted both right and left by one pixel to accommodate any small shifts in the positioning of the character on the uniform image. Columns with O-pixels are not assigned any margin, however columns with O-pixels that are directly to the left of columns that do contain pixels may be ignored entirely. This may be done to ensure that O-pixel columns factor into the statement, while also allowing for some variance with respect to placement of the character along the X,Y axis. In the image 472 shown in FIG. 25, we see the range of pixels that are being searched for in this example. Ignored columns are so indicated in FIG. 25. If a match is found, go to Step 14. If no match is found and this is not a split-image, go to Step 15. If no match is found and this is not a split-image, go to Step 16. Once again, this image is created solely for the purposes of visualization.

Step 14: Pattern Matching Algorithm. The broad MySQL (or other database application) statement will pull a number of entries from the database, some more accurate than others. At this point, another algorithm is run to see which database entry most closely matches the current character. As illustrated by images 474 and 476 in FIG. 26, one method for matching is to compare the deviation in the number of pixels in each row of the image and the database entry. The application also subtracts the number of black pixels in the image from the number of coordinates in the database histogram/2. In both the deviation and pixel comparison results, the closer to zero, the better the match. The following distance formula may be used to determine the best match:

$$\text{distance} = \text{square root}((a1_1 + a1_2)^2 + (a2_1 + a2_2)^2 + (a3_1 + a3_2)^2 + \ldots + (a40_1 + a40_2)^2)$$

Go to Step 17.

Step 15: Split image and find matches. In some instances, as shown for example in FIG. 27, letters and numbers are close together and thus may be interpreted as a single character by the application when bounding the letters (see Step 8 above). Working back and forth from the horizontal center of the image, split the image and repeat Steps 9-14 for halves of the image. Repeat this process until either a match is found for both sides of the split image, or until the right or left side of the image is reached. If there's a match for both sides of the image, go to Step 17. If not, go to Step 16.

Step 16: Add to Training Data Queue. If there is no match for the character in question, add the character's information and histogram into the database and set it to unapproved. Record the character's unique database ID number and embed it into a special character that is to be returned as output. Go to Step 17. The training data queue is comprised of unapproved characters. By being able to add to the training data, the application will always get better at interpreting data and can accommodate future changes, such as changing the font face. A user can go to the training data administration page and input the correct alphanumeric character. Once the character is entered, set the character to approved status in the database. If the special character that was previously returned by this application has been stored in the database, switch out the special character for the one entered by the user. Some embodiments may include an option to email an administrator when a new character has been entered.

Step 17: Return output. Once the best match has been determined (Step 14) or a special database identifier established (Step 16), return this text information to the larger application for interpretation, viewing and/or storage in the database.

Certain embodiments of computer programs directed to the foregoing processes are shown in the attached Appendix, which is incorporated herein by reference. All of the methods disclosed herein may be performed, in whole or in part, by one or more computer programs embodied in one or more computer readable mediums.

Although the foregoing specific details describe certain embodiments of this invention, persons reasonably skilled in the art will recognize that various changes may be made in the details of this invention without departing from the spirit and scope of the invention as defined in the appended claims and considering the doctrine of equivalents. Therefore, it should be understood that this invention is not to be limited to the specific details shown and described herein.

What is claimed is:

1. A computer-implemented method comprising:
   uploading digital image data from a digital data storage medium to a computer for each of a plurality of patients,
      said digital image data comprising an orthopedic image associated with an orthopedic surgical procedure performed on each of said plurality of patients by a plurality of surgeons,
      said orthopedic image comprising a graphics portion and a text portion,
      said text portion comprising a representation of an anatomical measurement parameter associated with said orthopedic surgical procedure and a representation of a value for said anatomical measurement parameter,
      said anatomical measurement parameter being selected from a distance between two anatomical features and an angle between two anatomical features;
   determining said value for said anatomical measurement parameter for each of said plurality of patients by executing an optical character recognition process on said text portion using a computer;
   storing said value for said anatomical measurement parameter for each of said plurality of patients in a computer-searchable database;
   receiving a query from an authorized user via a computer, said query comprising a search criterion comprising a value for said anatomical measurement parameter; and
   in response to said query, sending a search result to said authorized user via a computer, said search result comprising at least one of
      (a) the value of said anatomical measurement parameter for each of said plurality of patients that meets said search criterion, and
      (b) a statistic of the values of said anatomical measurement parameter for all of said plurality of patients that meet said search criterion;
   wherein at least one of said plurality of patients has no relationship with said authorized user and wherein said search result is configured to protect the privacy of said at least one of said plurality of patients with respect to said authorized user.

2. The method of claim 1 wherein said orthopedic surgical procedure comprises knee surgery and said anatomical measurement parameter is selected from extension gap, flexion gap, gap differential, varus angle, and valgus angle.

3. The method of claim 1 wherein said statistic is selected from average, mean, median, and standard deviation.

4. The method of claim 1 wherein said search criterion comprises a range of values for said anatomical measurement parameter.

5. The method of claim 1 further comprising:
   receiving surgical result data at a computer for each of said plurality of patients,
      said surgical result data comprising a value for a surgical result parameter associated with said orthopedic surgical procedure,
      said surgical result parameter being selected from range of motion, pain level, pain medication used, movement of implant, loosening of implant, degradation of implant, instances of repeated or additional operations, and elapsed time between operations;
   wherein said search result further comprises at least one of
      (a) the value of said surgical result parameter for each of said plurality of patients that meets said search criterion, and (b) a statistic of the values of said surgical result parameter for all of said plurality of patients that meet said search criterion.

6. The method of claim 5 wherein said statistic of the values of said surgical result parameter is selected from average, mean, median, and standard deviation.

* * * * *